US012758417B2

(12) United States Patent
Nishiura et al.

(10) Patent No.: US 12,758,417 B2
(45) **Date of Patent: *Oct. 13, 2026**

(54) MOTORIZED BEDDING SYSTEM AND APPLICATION SOFTWARE

(71) Applicant: PARAMOUNT BED CO., LTD., Tokyo (JP)

(72) Inventors: Sota Nishiura, Tokyo (JP); Tomokazu Nikaido, Tokyo (JP); Junko Nishimura, Tokyo (JP); Shinnosuke Kubota, Tokyo (JP); Toshihide Shiino, Tokyo (JP); Makoto Tanaka, Tokyo (JP)

(73) Assignee: PARAMOUNT BED CO., LTD., Tokyo (JP)

(*) Notice: Subject to any disclaimer, the term of this patent is extended or adjusted under 35 U.S.C. 154(b) by 17 days.

This patent is subject to a terminal disclaimer.

(21) Appl. No.: 18/937,614

(22) Filed: Nov. 5, 2024

(65) Prior Publication Data

US 2025/0057686 A1 Feb. 20, 2025

Related U.S. Application Data

(63) Continuation of application No. 17/326,743, filed on May 21, 2021, now Pat. No. 12,171,686.

(30) Foreign Application Priority Data

Oct. 19, 2020 (JP) ................................ 2020-175602

(51) Int. Cl.
*A61F 5/56* (2006.01)
*A47C 20/04* (2006.01)
(Continued)

(52) U.S. Cl.
CPC .............. *A61F 5/56* (2013.01); *A47C 20/041* (2013.01); *A47C 27/083* (2013.01); *A47C 27/10* (2013.01);
(Continued)

(58) Field of Classification Search
CPC ......... A61F 5/56; A47C 20/041; A47C 20/04; A47C 27/083; A47C 27/082;
(Continued)

(56) References Cited

U.S. PATENT DOCUMENTS 10,314,407 B1 6/2019 Main et al.
11,224,294 B2 1/2022 Nava
(Continued)

FOREIGN PATENT DOCUMENTS

CN 108420228 8/2018
CN 108784127 11/2018
(Continued)

*Primary Examiner* — Robert G Santos
(74) *Attorney, Agent, or Firm* — Wenderoth, Lind & Ponack, L.L.P.

(57) ABSTRACT

A motorized bedding system includes: an acquisition unit that is capable of acquiring a setting of motorized bedding of each of users, a state of each of the users, and snoring detection information of each of the users; a computation unit that is configured to compute a sleep score based on the state of each of the users; a memory that is configured to store data including multiple sets of the setting of the motorized bedding and the sleep score associated with each of the multiple sets of the setting; and an output unit that is configured to output a recommendation setting of the motorized bedding based on the setting associated with the high-level sleep score among the multiple sleep scores stored in the memory, in which the motorized bedding system includes: a first mode where the system automatically changes the setting of the motorized bedding based on the state of each of the users; and a second mode where the (Continued)

system automatically changes the setting of the motorized bedding based on the snoring detection information of each of the users and, in the case where both the first mode and the second mode are activated for a certain user out of the multiple users, upon acquiring the snoring detection information of the certain user, the motorized bedding system prioritizes the second mode over the first mode for the certain user.

18 Claims, 17 Drawing Sheets

(51) Int. Cl.

| | |
|---|---|
| ***A47C 27/08*** | (2006.01) |
| ***A47C 27/10*** | (2006.01) |
| ***G05B 15/02*** | (2006.01) |
| ***G06F 3/16*** | (2006.01) |
| *G05B 15/00* | (2006.01) |

(52) U.S. Cl.
CPC ............... *G05B 15/02* (2013.01); *G06F 3/16* (2013.01); *A47C 20/04* (2013.01); *A47C 27/081* (2013.01); *A47C 27/082* (2013.01); *G05B 15/00* (2013.01)

(58) Field of Classification Search
CPC ....... A47C 27/081; A47C 27/08; A47C 27/10; G05B 15/02; G05B 15/00; G06F 3/16
USPC ............................ 5/616, 600, 710, 713, 706
See application file for complete search history.

(56) References Cited

U.S. PATENT DOCUMENTS

| | | | | | |
|---|---|---|---|---|---|
| 11,350,758 | B2 | 6/2022 | Nava | | |
| 11,382,534 | B1 | 7/2022 | Kahn | | |
| 11,690,461 | B2 * | 7/2023 | Sayadi | A47C 27/10 | 700/282 |
| 12,042,050 | B2 | 7/2024 | Nava | | |
| 12,082,703 | B2 * | 9/2024 | Sayadi | A47C 27/083 | |
| 12,171,686 | B2 * | 12/2024 | Nishiura | A47C 27/10 | |
| 2003/0110565 | A1 | 6/2003 | Grabe | | |
| 2010/0011505 | A1 | 1/2010 | Horitani | | |
| 2014/0277822 | A1 | 9/2014 | Nunn et al. | | |
| 2018/0103768 | A1 | 4/2018 | Nava | | |
| 2018/0103769 | A1 | 4/2018 | Nava | | |
| 2018/0103770 | A1 | 4/2018 | Nava | | |
| 2018/0184811 | A1 | 7/2018 | Nava et al. | | |
| 2018/0338625 | A1 | 11/2018 | Nava | | |
| 2020/0205580 | A1 | 7/2020 | Sayadi et al. | | |
| 2020/0253384 | A1 | 8/2020 | Kubota et al. | | |
| 2020/0405526 | A1 | 12/2020 | Yu et al. | | |
| 2021/0282566 | A1 | 9/2021 | Nava | | |
| 2022/0117776 | A1 | 4/2022 | Nishiura | | |
| 2023/0404282 | A1 * | 12/2023 | Sayadi | A47C 31/008 | |
| 2024/0138586 | A1 | 5/2024 | Bennett | | |
| 2024/0407563 | A1 * | 12/2024 | Sayadi | A61B 5/0022 | |
| 2025/0057686 | A1 * | 2/2025 | Nishiura | A47C 20/041 | |

FOREIGN PATENT DOCUMENTS

| | | | | | |
|---|---|---|---|---|---|
| CN | 108814123 | | 11/2018 | | |
| EP | 3905927 | B1 * | 8/2023 | A47C 31/008 | |
| JP | 2008-220603 | | 9/2008 | | |
| JP | 2013-45336 | | 3/2013 | | |
| JP | 2016-518159 | | 6/2016 | | |
| JP | 2019-51070 | | 4/2019 | | |
| JP | 2019-155072 | | 9/2019 | | |
| JP | 2020-000306 | | 1/2020 | | |
| JP | 2020-110560 | | 7/2020 | | |
| WO | 2014/151753 | | 9/2014 | | |
| WO | 2019/107660 | | 6/2019 | | |
| WO | WO-2020142452 | A1 * | 7/2020 | G16H 40/67 | |

* cited by examiner

*FIG. 7*

TD D1a D1b D1c D3 D5

| | IDENTIFICATION INFORMATION | ATTRIBUTE INFORMATION | PREFERRED HARDNESS | MATTRESS SETTING | | | SLEEP SCORE |
|---|---|---|---|---|---|---|---|
| | | | | HARDNESS OF U1 | ... | HARDNESS OF U6 | |
| CATEGORY 1 | *** | *** | HARD | ** | ... | ** | 45 |
| | | | | ** | ... | ** | 50 |
| | | | | ** | ... | ** | 55 |
| | *** | *** | SOFT | ** | ... | ** | 85 |
| | | | | ** | ... | ** | 90 |
| | | | | ** | ... | ** | 95 |
| | *** | *** | NORMAL | ** | ... | ** | 98 |
| | | | | ** | ... | ** | 75 |
| | | | | ** | ... | ** | 80 |
| CATEGORY 2 | *** | *** | HARD | ** | ... | ** | 45 |
| | | | | ** | ... | ** | 50 |
| | | | | ** | ... | ** | 55 |
| | *** | *** | SOFT | ** | ... | ** | 85 |
| | | | | ** | ... | ** | 90 |
| | | | | ** | ... | ** | 95 |
| | *** | *** | NORMAL | ** | ... | ** | 70 |
| | | | | ** | ... | ** | 75 |
| | | | | ** | ... | ** | 80 |
| ⋮ | ⋮ | ⋮ | ⋮ | ⋮ | ⋮ | ⋮ | ⋮ |

CA CA DR D2b D2 D2a

FIG. 11

TD2, D1a, D1b, D1c, D22, D23, CA

| | IDENTIFICATION INFORMATION | ATTRIBUTE INFORMATION | PREFERRED HARDNESS | MATTRESS SETTING: HARDNESS OF U1 | MATTRESS SETTING: . . . | MATTRESS SETTING: HARDNESS OF U6 | BED SETTING: ANGLE OF BACK SECTION | BED SETTING: . . . | BED SETTING: ANGLE OF LOWER LEG SECTION | PILLOW SETTING: HEIGHT OF AIR CELL | PILLOW SETTING: . . . | PILLOW SETTING: HEIGHT OF AIR CELL | SLEEP SCORE |
|---|---|---|---|---|---|---|---|---|---|---|---|---|---|
| CATEGORY 1 | *** | *** | HARD | ** | . . . | ** | ** | . . . | ** | ** | . . . | ** | 45 |
| | | | | ** | . . . | ** | ** | . . . | ** | ** | . . . | ** | 50 |
| | | | | ** | . . . | ** | ** | . . . | ** | ** | . . . | ** | 55 |
| | *** | *** | SOFT | ** | . . . | ** | ** | . . . | ** | ** | . . . | ** | 85 |
| | | | | ** | . . . | ** | ** | . . . | ** | ** | . . . | ** | 90 |
| | | | | ** | . . . | ** | ** | . . . | ** | ** | . . . | ** | 95 |
| | *** | *** | NORMAL | ** | . . . | ** | ** | . . . | ** | ** | . . . | ** | 70 |
| | | | | ** | . . . | ** | ** | . . . | ** | ** | . . . | ** | 75 |
| | | | | ** | . . . | ** | ** | . . . | ** | ** | . . . | ** | 80 |
| CATEGORY 2 | *** | *** | HARD | ** | . . . | ** | ** | . . . | ** | ** | . . . | ** | 45 |
| | | | | ** | . . . | ** | ** | . . . | ** | ** | . . . | ** | 50 |
| | | | | ** | . . . | ** | ** | . . . | ** | ** | . . . | ** | 55 |
| | *** | *** | SOFT | ** | . . . | ** | ** | . . . | ** | ** | . . . | ** | 85 |
| | | | | ** | . . . | ** | ** | . . . | ** | ** | . . . | ** | 90 |
| | | | | ** | . . . | ** | ** | . . . | ** | ** | . . . | ** | 95 |
| | *** | *** | NORMAL | ** | . . . | ** | ** | . . . | ** | ** | . . . | ** | 70 |
| | | | | ** | . . . | ** | ** | . . . | ** | ** | . . . | ** | 75 |
| | | | | ** | . . . | ** | ** | . . . | ** | ** | . . . | ** | 80 |
| . . . | . . . | . . . | . . . | . . . | . . . | . . . | . . . | . . . | . . . | . . . | . . . | . . . | . . . |

MOTORIZED BEDDING SYSTEM AND APPLICATION SOFTWARE

CROSS-REFERENCE TO RELATED APPLICATIONS

The present application is a continuation of U.S. application Ser. No. 17/326,743, filed May 21, 2021, now U.S. Pat. No. 12,171,686, which claims the benefit of priority of Japanese Patent Application No. 2020-175602, filed on Oct. 19, 2020, the entire contents of which are incorporated herein by reference.

FIELD

An embodiment of this disclosure relates to a motorized bedding system and application software.

BACKGROUND

Heretofore, a motorized bed capable of changing the setting of parameters such as a section angle has been known. The quality of sleep of a user changes according to the setting of motorized bedding such as a motorized bed.

BRIEF DESCRIPTION OF THE DRAWINGS

FIG. 7 is a chart illustrating data stored in the server in the first embodiment.

FIG. 11 is a chart illustrating data stored in a server in the second embodiment.

DETAILED DESCRIPTION

Figure 1A:
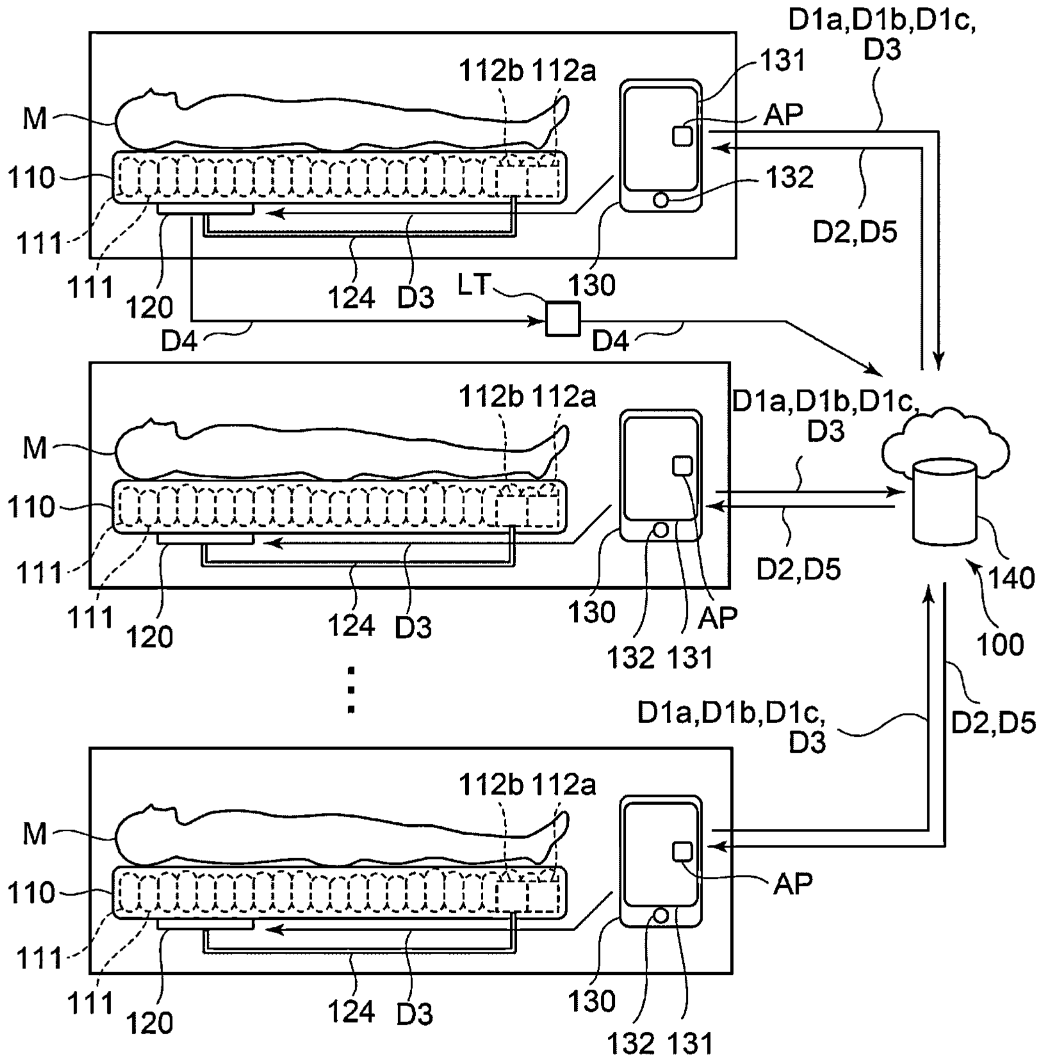
FIG. 1A is a conceptual diagram illustrating a motorized bedding system according to a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a motorized bedding system including: an acquisition unit that is capable of acquiring a setting of motorized bedding of each of users, a state of each of the users, and snoring detection information of each of the users; a computation unit that is configured to compute a sleep score based on the state of each of the users; a memory that is configured to store data including multiple sets of the setting of the motorized bedding and the sleep score associated with each of the multiple sets of the setting; and an output unit that is configured to output a recommendation setting of the motorized bedding based on the setting associated with the high-level sleep score among the multiple sleep scores stored in the memory. The motorized bedding system includes: a first mode in which the system automatically changes the setting of the motorized bedding based on the state of each of the users; and a second mode in which the system automatically changes the setting of the motorized bedding based on the snoring detection information of each of the users. In the case where both the first mode and the second mode are activated for a certain user out of the multiple users, upon acquiring the snoring detection information of the certain user, the motorized bedding system prioritizes the second mode over the first mode for the certain user.

Another aspect of the present application is application software including receiving input from a user on a setting of motorized bedding and sends the input setting of the motorized bedding to a server, detecting snoring of the user, and sends snoring detection information of the user to the server upon detecting the snoring of the user, acquiring recommendation setting of the motorized bedding from the server and presenting the acquired recommendation setting to the user, receiving input on whether or not to activate a first mode in which the setting of the motorized bedding is changed automatically based on a state of the user and whether or not to activate a second mode in which the setting of the motorized bedding is changed automatically based on the snoring detection information of the user, and sending the server an input result on whether or not the first mode is activated and whether or not the second mode is activated.

First Embodiment

Firstly, a first embodiment is described.

Figure 1B:
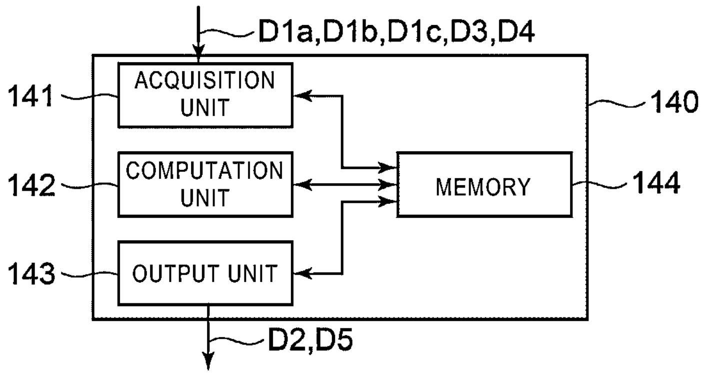
FIG. 1B is a block diagram illustrating functions of a server in the motorized bedding system according to the first embodiment.

FIG. 1A is a conceptual diagram illustrating a motorized bedding system according to this embodiment, and FIG. 1B is a block diagram of a server in the motorized bedding system according to this embodiment.

A motorized bedding system 100 according to this embodiment is used by multiple users M. In this embodiment, each user M has a mattress 110 (motorized bedding), a detector 120, and a user interface terminal 130. The user interface terminal 130 of each user M is capable of communicating with a server 140. Hereinbelow, parts of the motorized bedding system 100 are described in detail.

First, the mattress 110 is described.

Figure 2:
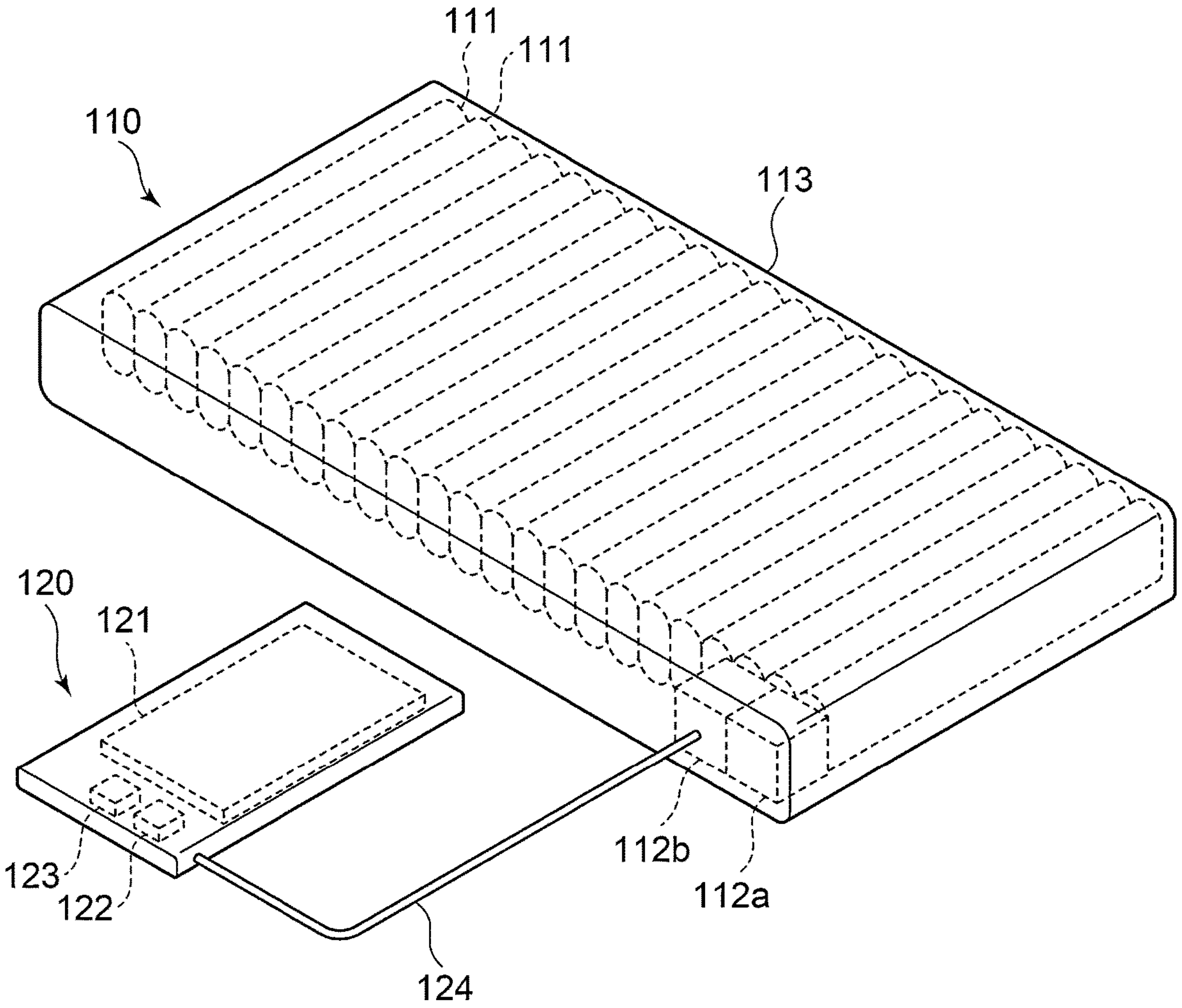
FIG. 2 is a perspective view illustrating a mattress and a detector in the motorized bedding system according to the first embodiment.

FIG. 2 is a perspective view illustrating the mattress and the detector in the motorized bedding system according to this embodiment.

Figure 3:
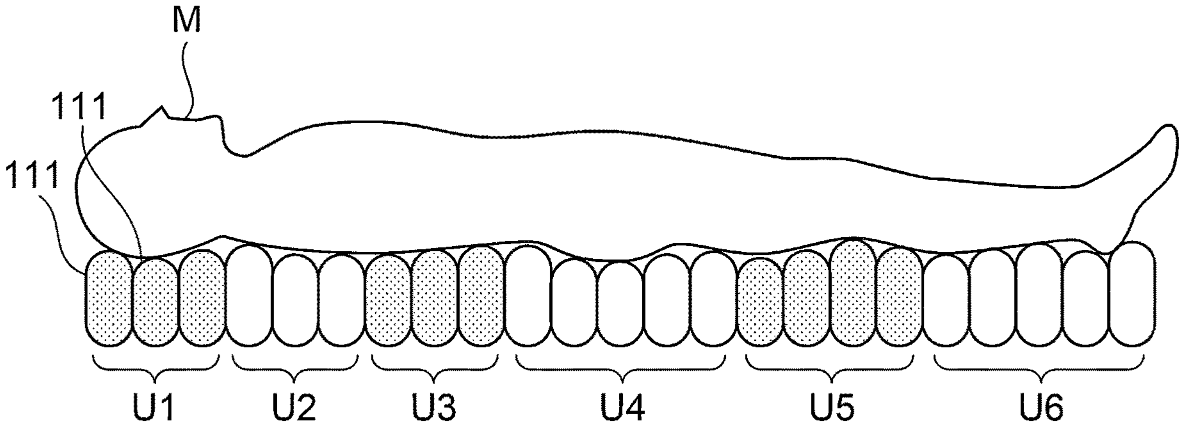
FIG. 3 is a side view illustrating air cells constituting the mattress.

FIG. 3 is a side view illustrating air cells constituting the mattress.

The mattress 110 is a mattress whose hardness is electrically adjustable. For example, the mattress 110 has multiple air cells 111, a driving unit 112*a*, a control unit 112*b*, and a cover 113.

The multiple air cells 111 are arranged in a direction extending from the head side of the mattress 110 toward the foot side thereof. Each air cell 111 extends in a lateral direction of the mattress 110.

As illustrated in FIG. 3, a part of the multiple air cells 111 constitutes a first air cell unit U1. The first air cell unit U1 is located right under a head part of the user M, for example. Another part of the multiple air cells 111 constitutes a second air cell unit U2. The second air cell unit U2 is located right under a shoulder part of the user M, for example.

Still another part of the multiple air cells 111 constitutes a third air cell unit U3. The third air cell unit U3 is located right under an abdomen of the user M, for example. Still another part of the multiple air cells 111 constitutes a fourth air cell unit U4. The fourth air cell unit U4 is located right under buttocks of the user M, for example.

Still another part of the multiple air cells 111 constitutes a fifth air cell unit U5. The fifth air cell unit U5 is located right under an upper leg part of the user M, for example. Still another part of the multiple air cells 111 constitutes a sixth air cell unit U6. The sixth air cell unit U6 is located right under a lower leg part of the user M, for example.

Note that, the number of air cell units constituting the mattress and the number of air cells constituting each air cell unit are not limited to the numbers illustrated in FIG. 2 and FIG. 3.

As illustrated in FIG. 2, the driving unit 112*a* includes a pump, for example.

The control unit 112*b* includes a circuit for controlling the driving unit 112*a*, for example. The control unit 112*b* is configured to control the driving unit 112*a* to adjust the volume of air inside each of the air cell units U1, U2, U3, U4, U5, and U6. Thereby, the control unit 112*b* can adjust the hardness of each of the air cell units U1, U2, U3, U4, U5, and U6.

The cover 113 houses the multiple air cells 111, the driving unit 112*a*, and the control unit 112*b*. The cover 113 may further house a cushion member (not illustrated). Here, the control unit may be located outside the cover.

Next, the detector 120 is described.

In this embodiment, the detector 120 is configured to acquire biological information including at least one of the body motion, heart rate, and breathing rate of the user M. In addition, the detector 120 is configured to judge, based on the biological information, the state of the user M such as the state of falling asleep, being half awake, or waking up.

For example, the method described in JP-A-2016-30177 (Title of Disclosure: Respiratory disturbance judgment device, respiratory disturbance judgment method, and program, Filing Date: Jul. 30, 2014) can be incorporated as a method of acquiring the biological information such as the heart rate and breathing rate. Alternatively, another publicly-known technique may also be used.

As illustrated in FIG. 2, the detector 120 includes a sensor 121, an analysis unit 122, and a communication unit 123. In this embodiment, the detector 120 is located below the mattress 110. However, the position of the detector 120 is not limited to the above position. The detector 120 may be located above the mattress.

The sensor 121 is a pressure sensor, for example.

The analysis unit 122 includes a processor such as a CPU (central processing unit) and a memory, for example. The analysis unit 122 is configured to extract (through frequency analysis, for example) biological information, including the body motion, heart rate, and breathing rate, based on a temporal change in pressure measured by the sensor 121. In addition, the analysis unit 122 is configured to presume, based on the biological information, the state of the user M such as the state of falling asleep, being half awake, or waking up.

However, the sensor does not necessarily have to be a pressure sensor as long as it can measure a signal from which the biological information can be extracted. For example, the sensor may be a load sensor. In addition, the detector may have multiple kinds of sensors.

The communication unit 123 is configured to perform wireless communication with the user interface terminal 130 and the server 140. As illustrated in FIG. 1A, the communication unit 123 is capable of communicating with the user interface terminal 130 through Bluetooth (registered trademark), for example. In addition, the communication unit 123 is capable of communicating with a router LT through Wi-Fi (registered trademark), for example. The router LT is capable of accessing a communication network such as the Internet. The communication unit 123 accesses the communication network and communicates with the server 140 via the router LT. However, the method of communication between the communication unit and the user interface terminal and the method of communication between the communication unit and the server are not limited to the above methods. In addition, the communication unit and the user interface terminal do not necessarily have to be capable of communicating with each other.

The communication unit 123 sends the server 140 detection information D4 detected by the detector 120. The detection information D4 includes the biological information and the result of judgment on the state of the user M.

Further, in this embodiment, the detector 120 is electrically connected to the control unit 112*b* of the mattress 110 through a cable 124. The control unit 112*b* communicates with the user interface terminal 130 and the server 140 via the communication unit 123 of the detector 120. However, the mattress may be provided with a communication unit for enabling the control unit of the mattress to communicate with the user interface terminal and the server. In addition, in this case, the detector does not necessarily have to have a communication unit and may communicate with the server and the user interface terminal via the communication unit of the mattress.

Note that, the system may have such a configuration that the detector 120 constitutes a part of the mattress 110.

Next, the user interface terminal 130 is described.

The user interface terminal 130 is a tablet type terminal such as a smartphone. The user interface terminal 130 includes a processor such as a CPU, a memory, a communication unit, a display 131, a user interface button 132, and the like.

The communication unit of the user interface terminal 130 is capable of accessing a communication network such as the Internet. The communication unit of the user interface terminal 130 accesses the communication network and communicates with the server 140. In addition, the user interface terminal 130 is capable of communicating with the detector 120 through Bluetooth (registered trademark), for example. However, the method of communication between the user interface terminal and the server is not limited to the above method.

Before using the mattress 110, the user M installs application software AP, which is designed to assist in the use of the mattress 110, in the user interface terminal 130 in advance. Hereinbelow, the application software AP that assists in the use of the mattress 110 is referred to as an auxiliary app AP. This auxiliary app AP includes a setting function of setting the hardness of each of the air cell units U1, U2, U3, U4, U5, and U6, a score display function of displaying the quality of sleep of the user M, and a recommendation function of recommending, based on the sleep information, the hardness of each of the air cell units U1, U2, U3, U4, U5, and U6 suitable for the user M.

After installing the auxiliary app AP in the user interface terminal 130, the user M carries out user registration first.

Figure 4A:
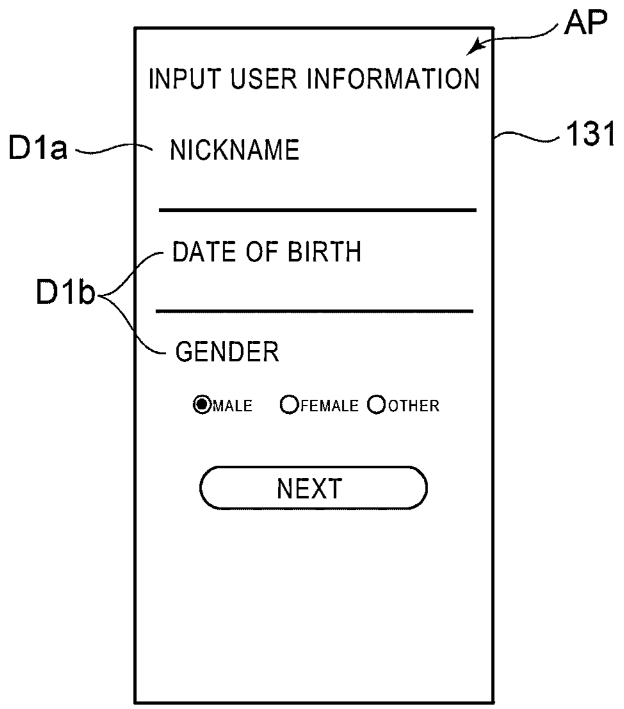
FIGS. 4A and 4B are diagrams illustrating user registration screens of an auxiliary app in the first embodiment.
Figure 4B:
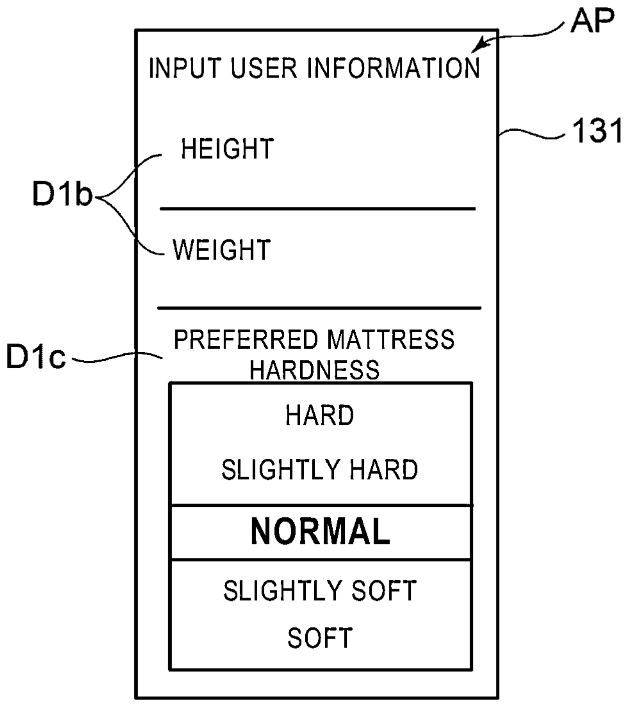

FIGS. 4A and 4B are diagrams illustrating user registration screens of the auxiliary app in this embodiment.

At the time of the user registration, the auxiliary app AP acquires identification information D1*a* and attribute information D1*b* of the user M and the user M's preferred hardness D1*c* of the mattress 110. In addition, the auxiliary app AP communicates with the detector 120 via the communication unit of the user interface terminal 130 to acquire information on the mattress 110 held by the user M.

For example, the identification information D1*a* is a nickname of the user M and the like. However, the identification information is not limited to the nickname and any information can be used as long as the user can be identified by this information.

For example, the attribute information D1*b* includes at least one of the age, gender, height, weight, and body mass index (BMI) of the user M. For example, as illustrated in FIG. 4A, the auxiliary app AP obtains the age of the user M by making the user M input his/her date of birth. In addition, the auxiliary app AP obtains the BMI of the user M by making the user input his/her height and weight, for example. However, the method of obtaining the attribute information is not limited to the above method.

The auxiliary app AP makes the user M select the preferred hardness D1*c* among 5 levels including "hard", "slightly hard", "normal", "slightly soft", and "soft". However, the method of acquiring the preferred hardness is not limited to the above method. In addition, the auxiliary app does not necessarily have to acquire the preferred hardness.

As illustrated in FIG. 1A, the auxiliary app AP sends the server 140 the identification information D1*a*, the attribute information D1*b*, the preferred hardness D1*c*, and the information on the mattress 110 held by the user M via the communication unit of the user interface terminal 130. Thereby, the user registration of the user M is completed. The user registration enables the user M to use the setting function, the score display function, and the recommendation function of the auxiliary app AP.

First, the setting function is described.

Figure 5A:
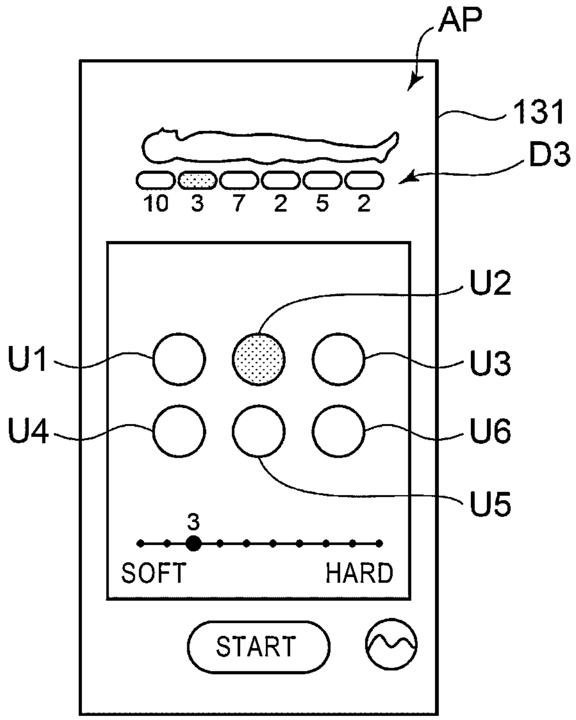
FIG. 5A is a diagram illustrating a mattress setting function of the auxiliary app in the first embodiment.
Figure 5B:
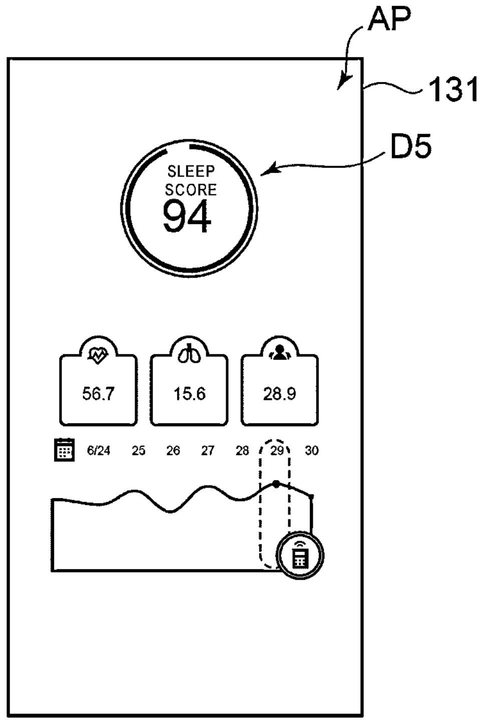
FIG. 5B is a diagram illustrating a score display function of the auxiliary app in the first embodiment.

FIG. 5A is a diagram illustrating the mattress setting function of the auxiliary app in this embodiment, and FIG. 5B is a diagram illustrating the score display function of the auxiliary app in this embodiment.

Using the auxiliary app AP, the user M can set the hardness of each of the air cell units U1, U2, U3, U4, U5, and U6. The auxiliary app AP expresses the hardness setting value of each of the air cell units U1, U2, U3, U4, U5, and U6 by use of 10-level numbers from 1 to 10, for example. This value denotes that the larger the number is, the harder the corresponding one of the air cells units U1, U2, U3, U4, U5, and U6 is. However, the method of expressing the hardness setting value is not limited to the above method and any method can be used as long as the user can understand the difference in hardness by this method. The auxiliary app AP makes the user M select and confirm the hardness setting value of each of the air cell units U1, U2, U3, 4, 5, and U6 among 10 levels.

The auxiliary app AP sends the confirmed setting D3 of the mattress 110, including the hardness setting value of each of the air cell units U1, U2, U3, U4, U5, and U6, to the server 140 via the communication unit of the user interface terminal 130. In addition, as illustrated in FIG. 1A, the auxiliary app AP sends the setting D3 of the mattress 110 to the detector 120 via the communication unit of the user interface terminal 130. The control unit 112*b* of the mattress 110 acquires the setting D3 of the mattress 110 from the detector 120. The control unit 112*b* controls the driving unit 112*a* based on the setting D3 to adjust the hardness of each of the air cell units U1, U2, U3, U4, U5, and U6. However, instead of causing the user interface terminal to send the mattress setting to the detector, the server may send the mattress setting, acquired from the user interface terminal, to the detector.

Note that, if the mattress further has a remote controller such as a handy switch, the user may adjust the hardness of each of the air cell units by manipulating the remote controller in addition to the user interface terminal. Further, the remote controller may send the server the mattress setting including the hardness setting value of each of the air cell units.

Next, the score display function of the auxiliary app AP is described.

As illustrated in FIG. 5B, the score display function indicates a function of displaying a sleep score D5 obtained when the user M is sleeping using the mattress 110. The sleep score D5 is a score for evaluating the quality of sleep of the user M. For example, the sleep score D5 indicates evaluation for the user M's series of sleep processes from the state of falling asleep to the state of waking up. The server 140 calculates the sleep score D5 of the user M and outputs it to the auxiliary app AP.

When waking up, the user M can check the sleep score D5 on the auxiliary app AP of the display 131.

The auxiliary app AP expresses the sleep score D5 by use of 100-level numbers from 1 to 100, for example. This score denotes that the larger the number is, the better the quality of sleep is. However, the method of expressing the sleep score is not limited to the above method and any method can be used as long as the user can understand the quality of sleep by this method.

Next, the recommendation function of the auxiliary app AP is described.

Figure 6:
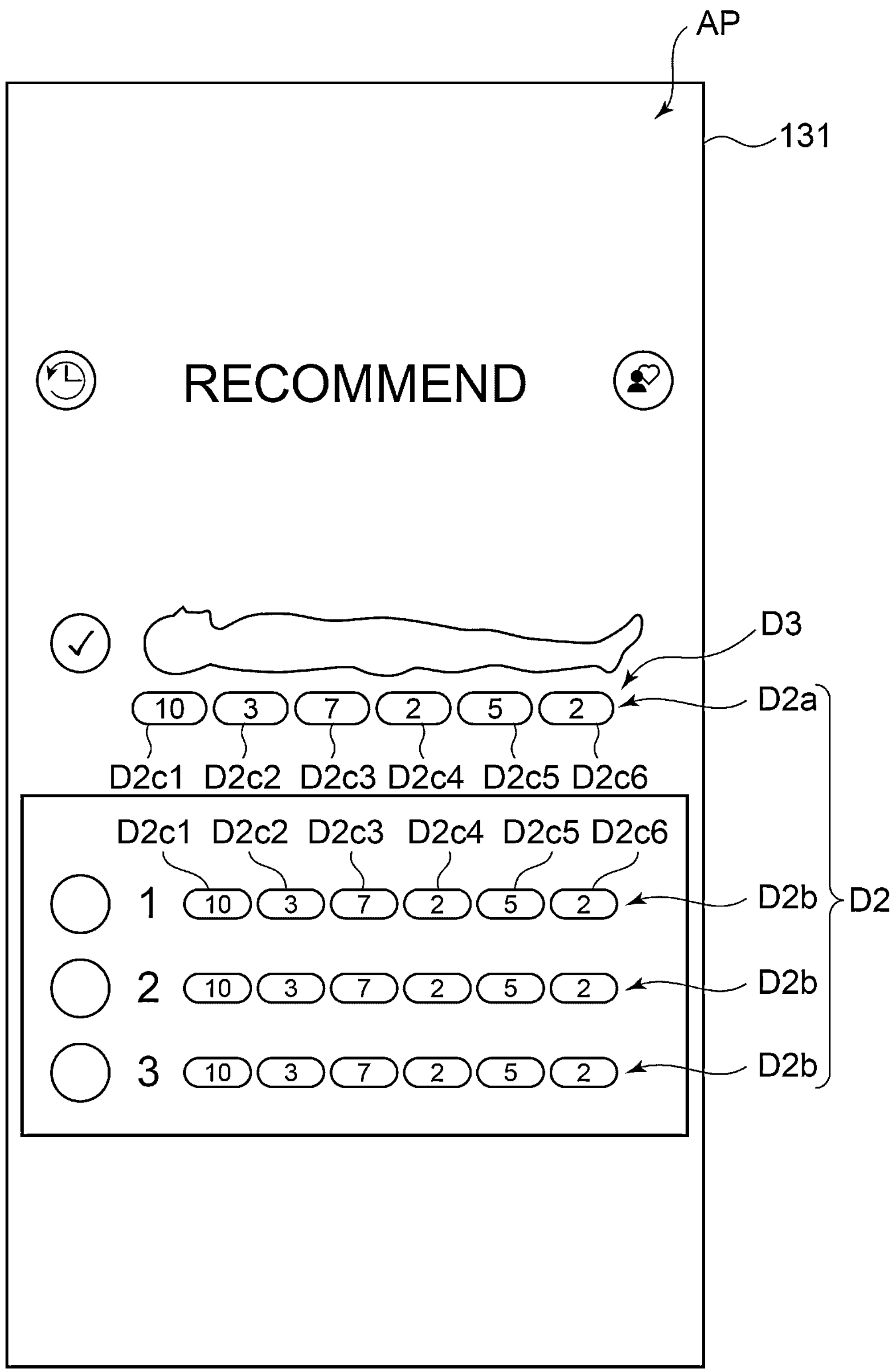
FIG. 6 is a diagram illustrating a recommendation function of the auxiliary app in the first embodiment.

FIG. 6 is a diagram illustrating the recommendation function of the auxiliary app in this embodiment.

The recommendation function indicates the auxiliary app AP's function of presenting the user M with recommendation setting D2 of the hardness of each of the air cell units U1, U2, U3, U4, U5, and U6 of the mattress 110. The user M can set the hardness of each of the air cell units U1, U2, U3, U4, U5, and U6 while referring to the recommendation setting D2. Here, the recommendation setting D2 is determined based on input information (such as the attribute information D1*b* and the preferred hardness D1*c*) of the user M who requests the recommendation setting D2 and sleep information (such as the sleep score D5 of the user M who requests the recommendation setting D2 and the sleep score D5 of another user M).

Based on the input information of the user M and the sleep information, the server 140 outputs the recommendation setting D2 of the user M to the auxiliary app AP.

As illustrated in FIG. 6, the auxiliary app AP displays the recommendation setting D2 of the mattress 110 on the display 131.

Hereinbelow, a specific description is given of how the recommendation setting D2 of the auxiliary app AP is displayed.

In this embodiment, the recommendation setting D2 includes first recommendation setting D2*a* and second recommendation setting D2*b*. The first recommendation setting D2*a* is determined by the server 140 based on the attribute information D1*b* of the user M, the user's preferred hardness D1*c*, and the sleep information. The second recommendation setting D2*b* is determined by the server 140 based on the attribute information D1*b* and the sleep information without consideration of the user M's preferred hardness D1*c*. The method of determining the first recommendation setting D2*a* and the second recommendation setting D2*b* are to be described later.

The auxiliary app AP presents multiple sets of the second recommendation setting D2*b* in the order of recommendation. However, the number of sets of the second recommendation setting D2*b* is not limited to that illustrated in FIG. 6. For example, the number of sets of the second recommendation setting may be one. In addition, the auxiliary app may present multiple sets of the first recommendation setting in the order of recommendation. Further, the auxiliary app may present only one of the first recommendation setting and the second recommendation setting.

Each of the first recommendation setting D2*a* and the second recommendation setting D2*b* includes recommended hardness D2*cl* of the first air cell unit U1, recommended hardness D2*c*2 of the second air cell unit U2, recommended hardness D2*c*3 of the third air cell unit U3, recommended hardness D2*c*4 of the fourth air cell unit U4, recommended hardness D2*c*5 of the fifth air cell unit U5, and recommended hardness D2*c*6 of the sixth air cell unit U6. In other words, the auxiliary app AP presents recommended hardness patterns for the multiple air cell units U1, U2, U3, U4, U5, and U6.

The auxiliary app AP expresses the recommended hardness D2*c*1, D2*c*2, D2*c*3, D2*c*4, D2*c*5, and D2*c*6 by use of 10-level numbers from 1 to 10, for example. This value denotes that the larger the number is, the harder the corresponding one of the air cells units U1, U2, U3, U4, U5, and U6 is. However, the method of expressing the hardness is not limited to the above method and any method can be used as long as the user can understand the difference in hardness by this method.

The user M determines the setting D3 of the mattress 110 while referring to the recommendation setting D2 displayed on the display 131. For example, as illustrated in FIG. 6, the user M may set one of the first recommendation setting D2*a* and the second recommendation setting D2*b* as the setting D3 of the mattress 110. Alternatively, the user M may modify one of the first recommendation setting D2*a* and the second recommendation setting D2*b* and set the modified setting as the setting D3 of the mattress 110. As illustrated in FIG. 1A, the auxiliary app AP sends the setting D3 of the mattress 110 to the server 140 via the communication unit of the user interface terminal 130. In addition, the auxiliary app AP sends the setting D3 of the mattress 110 to the detector 120 via the communication unit of the user interface terminal 130. The control unit 112*b* of the mattress 110 acquires the setting D3 of the mattress 110 from the detector 120. The control unit 112*b* controls the driving unit 112*a* based on the setting D3 to adjust the hardness of each of the air cell units U1, U2, U3, U4, U5, and U6.

In this way, the user M may determine the setting D3 of the mattress 110 using the setting function of the auxiliary app AP, or alternatively may determine the setting D3 of the mattress 110 while referring to the recommendation setting D2 using the recommendation function.

Note that, the auxiliary app AP does not necessarily have to be installed in the user interface terminal of the user. For example, if the mattress has a remote controller with a display, the auxiliary app may be installed in the remote controller of the mattress.

Next, the server 140 is described.

The server 140 is a cloud server, for example. The server 140 includes a processor such as a CPU, a memory, a communication unit, and the like. As illustrated in FIG. 1B, in this embodiment, the server 140 has functions as an acquisition unit 141 that is configured to acquire various kinds of information from the detector 120 and the user interface terminal 130, a computation unit 142 that is configured to carry out computation such as calculation of the sleep score D5 and determination of the recommendation setting D2, an output unit 143 that is configured to output various kinds of information to the detector 120 and the user interface terminal 130, and a memory 144 that is configured to store various kinds of information. Hereinbelow, the various functions of the server 140 are described.

FIG. 7 is a chart illustrating data stored in the server in this embodiment.

The memory 144 stores data TD. The data TD is data in the form of a table, for example. The data TD has, for each user M, an item of the identification information D1*a*, an item of the attribute information D1*b*, an item of the preferred hardness D1*c*, an item of the setting D3 of the mattress 110, and an item of the sleep score D5.

At the time of the user registration, the acquisition unit 141 acquires the identification information D1*a*, the attribute information D1*b*, and the preferred hardness D1*c* from the auxiliary app AP. The data TD is classified into multiple categories CA. The computation unit 142 classifies the users M so that the users M having similar attribute information D1*b* belong to the same category CA. According to the classification result, the computation unit 142 stores the acquired identification information D1*a*, attribute information D1*b*, and preferred hardness D1*c* in the data TD.

In addition, the acquisition unit 141 acquires the setting D3 of the mattress 110 from the auxiliary app AP every time the user M determines the setting D3 using the setting function or the recommendation function of the auxiliary app AP. The computation unit 142 updates the data TD so that the acquired setting D3 of the mattress 110 is associated with the identification information D1*a* of the corresponding user M.

Note that, the user M may change the attribute information D1*b* in the auxiliary app AP. In this case, the computation unit 142 re-classifies this user M to one of the multiple categories CA based on the attribute information D1*b* thus changed. The computation unit 142 stores the identification information D1*a*, the changed attribute information D1*b*, and the preferred hardness D1*c* of this user M in the re-classified category CA of the data TD. In this event, the computation unit 142 may leave, in the data TD, the attribute information D1*b*, the preferred hardness D1*c*, and the setting D3 of the mattress 110 of this user M which have been acquired before the change. In this case, the computation unit 142 stores the setting D3 of the mattress 110 of this user M, which has been acquired after the change, in the re-classified latest category CA of the data TD.

Likewise, the user M may change the preferred hardness D1*c* in the auxiliary app AP. In this case, the computation unit 142 stores the preferred hardness D1*c* thus changed in the data TD. In this event, the computation unit 142 may leave, in the data TD, the preferred hardness D1*c* and the setting D3 of the mattress 110 of this user M which have been acquired before the change. Then, the computation unit 142 may store the setting D3 of the mattress 110 of this user M, which has been acquired after the change, in the data TD so that this setting is associated with the preferred hardness D1*c* thus changed.

In addition, the acquisition unit 141 acquires the detection information D4 of the detector 120 at predetermined time intervals at least during the time since the user M goes to bed until the user wakes up. The memory 144 stores the detection information D4. After the detector 120 detects that the user M has woken up, the computation unit 142 calculates, based on the series of detection information D4, the sleep score D5 associated with the setting D3 of the mattress 110.

Specifically, based on the detection information D4, the computation unit 142 presumes the time required since the user M goes to bed until the user falls asleep, whether or not the user is half awake, total sleep time, the number of body motions, the number of times the user moves away from the bed, and the like. The computation unit 142 calculates the sleep score D5 based on the result of presumption.

For example, the method described in Japanese Patent No. 5749121 (Title of Disclosure: Sleep state evaluation device, sleep state evaluation system, and program, Filing Date: Aug. 25, 2011) can be incorporated as a method of calculating the sleep score D5. Alternatively, another publicly-known technique may also be used.

After calculating the sleep score D5, the computation unit 142 updates the data TD so that the sleep score D5 is associated with the corresponding setting D3 of the mattress 110. In addition, the output unit 143 sends the sleep score D5 to the user interface terminal 130.

Accordingly, for one user M, the setting D3 of the mattress 110 and the sleep score D5 are stored in the data TD according to the number of times the mattress 110 and the auxiliary app AP are used. To put it differently, a use record DR including the setting D3 of the mattress 110 and the sleep score D5 of each user M are stored in the data TD.

When the auxiliary app AP requests the recommendation setting D2, the computation unit 142 determines the recommendation setting D2 based on the input information of the user M and the sleep information.

In this embodiment, the computation unit 142 sets, as the first recommendation setting D2*a*, the setting D3 associated with the largest sleep score D5 among the sets of the setting D3 in the group of the users M who belong to the same category CA and have the same preferred hardness D1*c* as the user M requesting the recommendation setting D2. In addition, without considering the preferred hardness D1*c*, the computation unit 142 sets, as the multiple sets of the second recommendation setting D2*b*, the multiple sets of the setting D3 associated with the higher-level sleep scores D5 among the sets of the setting D3 of the users M who belong to the same category CA as the user M requesting the recommendation setting D2.

The computation unit 142 may previously set the first recommendation setting D2*a* for each of combinations of the category CA and the preferred hardness D1*c*. In addition, the computation unit 142 may previously set the second recommendation setting D2*b* for each category CA. In this case, the computation unit 142 extracts, among the multiple sets of the recommendation setting D2 thus set, the recommendation setting D2 according to the attribute information D1*b* and the preferred hardness D1*c* of the user M. Alternatively, the computation unit 142 may extract, from the data TD, the recommendation setting D2 according to the attribute information D1*b* and the preferred hardness D1*c* of the user M every time the auxiliary app AP requests the recommendation setting D2.

However, the method of determining the recommendation setting is not limited to the above methods. For example, the server may set, as the recommendation setting, the setting associated with the high-level sleep score among the sets of the setting included in the use record. Alternatively, for example, if judging that the number of body motions of the user tends to be small based on the sleep information (detection information) acquired when the mattress was used in the past, the server may set, as the recommendation setting, the setting in which the hardness of each of the air cell units is set harder than that in the setting employed in the past use record.

Next, operations of the motorized bedding system 100 according to this embodiment are described.

Figure 8:
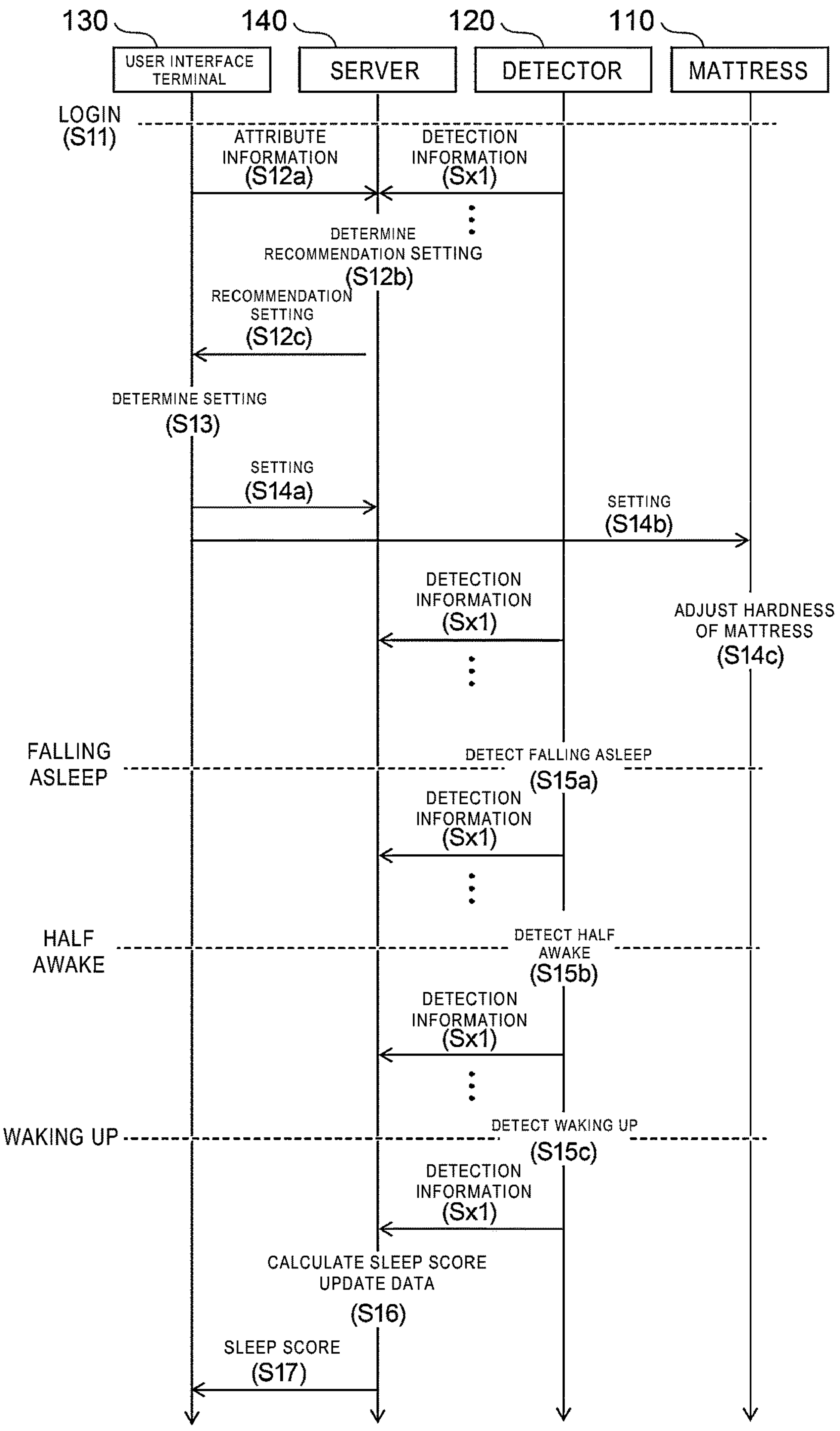
FIG. 8 is a sequence diagram illustrating operations of the motorized bedding system according to the first embodiment.

FIG. 8 is a sequence diagram illustrating the operations of the motorized bedding system according to this embodiment.

Note that, the operations of the motorized bedding system 100 described below are an example. The constituents executing the operations of the motorized bedding system, the timings at which these operations are executed, and the order in which these operations are executed can vary depending on the configuration of the motorized bedding system. In the sequence of FIG. 8, for the sake of convenience of description, it is assumed that the user M's user registration is completed already.

The user M logs into the auxiliary app AP in the user interface terminal 130 if wanting to set up the mattress 110 using the recommendation function of the auxiliary app AP (Step S11). In the following process, the detector 120 sends the detection information D4 to the server 140 at predetermined time intervals, and the memory 144 of the server 140 stores the received detection information D4 (Step Sx1).

Next, the auxiliary app AP in the user interface terminal 130 sends the identification information D1*a*, the attribute information D1*b*, and the preferred hardness D1*c* of the user M to the server 140 (Step S12*a*). Note that, the user interface terminal may send only the identification information of the user to the server.

Subsequently, the computation unit 142 of the server 140 determines the recommendation setting D2 according to the input information and the sleep information (Step S12*b*). Specifically, in this embodiment, the computation unit 142 of the server 140 determines the first recommendation setting D2*a* based on the attribute information D1*b* and the preferred hardness D1*c* of the user M and the sleep information including the sleep scores D5 of the multiple users M. In addition, the computation unit 142 of the server 140 determines the multiple sets of the second recommendation setting D2*b* based on the attribute information D1*b* of the user M and the sleep information including the sleep scores D5 of the multiple users M without considering the preferred hardness D1*c*.

Next, the output unit 143 of the server 140 outputs the recommendation setting D2 to the user interface terminal 130 (Step S12*c*).

Subsequently, the auxiliary app AP in the user interface terminal 130 displays the recommendation setting D2 on the display 131 to make the user M determine the setting D3 of the mattress 110 (Step S13).

Next, the auxiliary app AP sends the setting D3 of the mattress 110 to the server 140 (Step S14*a*). The acquisition unit 141 of the server 140 updates the data TD so that the setting D3 of the mattress 110 is associated with the identification information D1*a* of the user M.

In addition, the auxiliary app AP sends the setting D3 of the mattress 110 to the control unit 112*b* of the mattress 110 (Step S14*b*).

Subsequently, the control unit 112*b* controls the driving unit 112*a* based on the setting D3 to adjust the hardness of each of the air cell units U1, U2, U3, U4, 5, and U6 (Step S14*c*). Thereby, the hardness of each of the air cell units U1, U2, U3, U4, U5, and U6 is adjusted to the hardness set by the user M. Next, the user M gets onto the mattress 110.

For example, when the user M has fallen asleep, the detector 120 judges that the user M has fallen asleep (Step S15*a*). In this case, the detector 120 sends the detection information D4 including the judgment result to the server 140 (Step Sx1).

Meanwhile, when the user M awakes after falling asleep for example, the detector 120 judges that the user M is half awake (Step S15*b*). In this case, the detector 120 sends the detection information D4 including the judgment result to the server 140 (Step Sx1).

Meanwhile, when the user M has woken up for example, the detector 120 judges that the user M has woken up (Step S15*c*). In this case, the detector 120 sends the detection information D4 including the judgment result to the server 140 (Step Sx1).

Upon receiving the result of judgment that the user M has woken up, the computation unit 142 of the server 140 calculates the sleep score D5 (Step S16). In addition, the computation unit 142 of the server 140 updates the data TD so that the sleep score D5 is associated with the corresponding setting D3 of the mattress 110.

Next, the server 140 sends the sleep score D5 to the user interface terminal 130 (Step S17). The user M can check the sleep score D5 on the auxiliary app AP in the user interface terminal 130.

Note that, the constituents executing the operations of the motorized bedding system are not limited to the above constituents. For example, when the auxiliary app is installed in a controller of the mattress, the controller of the mattress may send the attribute information and the setting of the mattress to the server and present the recommendation setting. In addition, the control unit of the mattress or the analysis unit of the detector may calculate the sleep score and send the sleep score to the server.

Further, the timings at which the operations of the motorized bedding system are executed are not limited to the above timings. For example, instead of sending the attribute information to the server when the user logs into the auxiliary app, the auxiliary app may send the attribute information to the server when the auxiliary app receives a recommendation setting request from the user. In addition, instead of calculating the sleep score when the user awakes, the server may calculate the sleep score when the auxiliary app receives a sleep score request from the user.

Next, effects of this embodiment are described.

In existing systems, although the hardness of the mattress 110 is adjustable, the user M has no information for making a judgment in order for the user to set the mattress 110 so that he/she can achieve high quality sleep. In particular, when the mattress 110 includes the multiple air cell units U1, U2, U3, U4, U5, and U6, there are various hardness patterns of the multiple air cell units U1, U2, U3, U4, U5, and U6. Accordingly, it is difficult for the user M to judge the hardness pattern that offers high quality sleep.

The motorized bedding system 100 according to this embodiment presents the user M with the recommendation setting D2 of the mattress 110 based on the input information of the user M and the sleep information. Thus, the user M can determine the setting D3 of the mattress 110 while referring to the recommendation setting D2. This enables the user M to set the mattress 110 more easily.

In addition, the motorized bedding system 100 presents, as the recommendation setting D2, the setting D3 associated with the high sleep score D5 among the sets of the setting D3 of the mattress 110 of the users M having similar attribute information D1*b* to that of the user M requesting the recommendation setting D2. Accordingly, by employing the recommendation setting D2, the user M becomes more likely to achieve high quality sleep. Due to the above, the motorized bedding system 100 can offer high quality sleep to the user M.

Further, the recommendation setting D2 includes the first recommendation setting D2*a* based on the attribute information D1*b* and the preferred hardness D1*c* of the user M and the second recommendation setting D2*b* based on the attribute information D1*b*. Accordingly, the user M can set the mattress 110 while referring to both the first recommendation setting D2*a* that is set in consideration of the preferred hardness D1*c* and the second recommendation setting D2*b* that is set without consideration of the preferred hardness D1*c*.

Second Embodiment

Next, a second embodiment is described.

Figure 9:
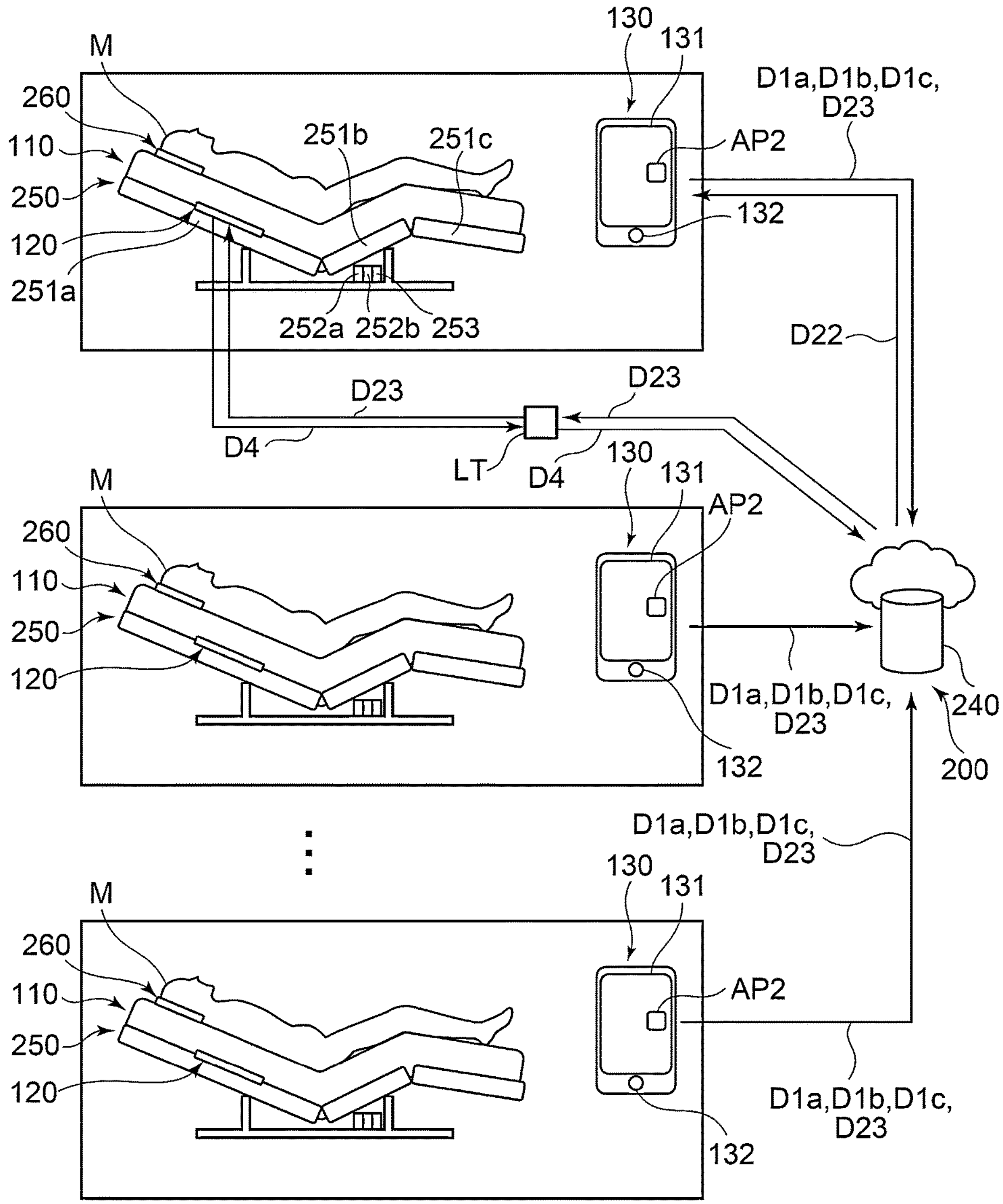
FIG. 9 is a conceptual diagram illustrating a motorized bedding system according to a second embodiment.

FIG. 9 is a conceptual diagram illustrating a motorized bedding system according to this embodiment.

A motorized bedding system 200 according to this embodiment differs from the motorized bedding system 100 according to the first embodiment in that an auxiliary app AP2 is capable of presenting recommendation setting D22 of the mattress 110 (bedding), a bed 250 (bedding), and a pillow 260 (bedding), and that the user M can select an automatic operation mode (a first mode) on the auxiliary app AP.

Note that, in the following description, basically only the points of difference from the first embodiment are described. Points other than those to be described below are the same as those of the first embodiment.

Hereinbelow, a description is given of an example in which each user M of the motorized bedding system 200 holds the mattress 110, the bed 250, and the pillow 260. However, not all the users have to hold the mattress, the bed, and the pillow. For example, there may be a user who holds only one or two of the mattress, the bed, and the pillow.

The bed 250 is a motorized bed. The bed 250 has a back section 251*a*, an upper leg section 251*b*, a lower leg section 251*c*, a driving unit 252*a*, a control unit 252*b*, and a communication unit 253. However, the number of sections constituting the bed is not limited to the number illustrated in FIG. 9. For example, the bed may further have a seat section.

The mattress 110 is located above the back section 251*a*, the upper leg section 251*b*, and the lower leg section 251*c*. The detector 120 is located between the mattress 110 and the back section 251*a*. However, the position of the detector is not limited to the above position.

The driving unit 252*a* includes an actuator, for example. The control unit 252*b* includes a circuit for controlling the driving unit 252*a*, for example. The control unit 252*b* controls the driving unit 252*a* to adjust the angle of the back section 251*a*, the angle of the upper leg section 251*b*, and the angle of the lower leg section 251*c* individually. Thereby, the control unit 252*b* can change the posture of the user M on the mattress 110.

The communication unit 253 is configured to perform wireless communication with the detector 120, the user interface terminal 130, and a server 240. The communication unit 253 is capable of communicating with the user interface terminal 130 through Bluetooth (registered trademark), for example. In addition, the communication unit 253 is capable of communicating with the router LT through Wi-Fi (registered trademark), for example. The communication unit 253 accesses the communication network and communicates with the server 240 via the router LT. However, the method of communication between the communication unit and the user interface terminal and the method of communication between the communication unit and the server are not limited to the above methods. The auxiliary app AP2 in the user interface terminal 130 communicates with the communication unit 253 and registers the bed 250 of the user M in advance.

Figure 10:
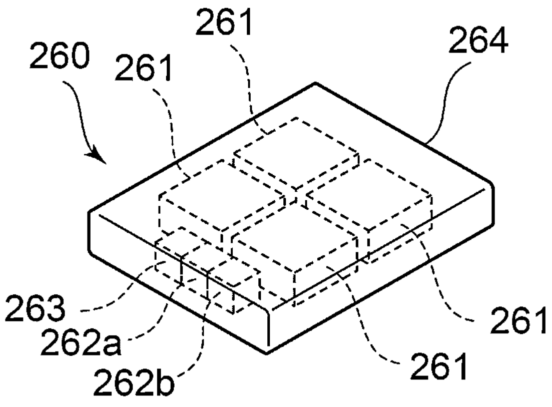
FIG. 10 is a perspective view illustrating a pillow in the second embodiment.

FIG. 10 is a perspective view illustrating the pillow in this embodiment.

For example, the pillow 260 has multiple air cells 261, a driving unit 262*a*, a control unit 262*b*, a communication unit 263, and a cover 264.

The multiple air cells 261 are arranged in a lateral direction of the pillow 260 and in a direction extending from the head side of the pillow toward the foot side thereof. The number of air cells constituting the pillow 260 is not limited to the number illustrated in FIG. 10. For example, the multiple air cells 261 may be arranged in a longitudinal direction of the pillow 260 and in a direction extending from the left side of the pillow toward the right side thereof. The multiple air cells 261 may alternatively be arranged in such a way that they are arranged in a partial area of the pillow 260 in the lateral direction of the pillow 260 and in the direction extending from the head side of the pillow toward the foot side thereof and, on the other hand, are arranged in another partial area of the pillow in the longitudinal direction of the pillow 260 and in the direction extending from the left side of the pillow toward the right side thereof.

The driving unit 262*a* includes a pump, for example.

The control unit 262*b* includes a circuit for controlling the driving unit 262*a*, for example. The control unit 262*b* is configured to control the driving unit 262*a* to adjust the volume of air inside each of the air cells 261. Thereby, the control unit 262*b* can adjust the height or hardness of each of the air cells 261. In addition, by adjusting the volume of air inside the air cells 261 arranged in the lateral direction or the volume of air inside the air cells 261 arranged from the head side toward the neck side, the control unit 262*b* can change the direction of the head of the user M on the pillow 260.

The communication unit 263 is configured to perform wireless communication with the detector 120, the user interface terminal 130, and the server 240. The communication unit 263 is capable of communicating with the user interface terminal 130 through Bluetooth (registered trademark), for example. In addition, the communication unit 263 is capable of communicating with the router LT through Wi-Fi (registered trademark), for example. The communication unit 263 accesses the communication network and communicates with the server 240 via the router LT. However, the method of communication between the communication unit and the user interface terminal and the method of communication between the communication unit and the server are not limited to the above methods. The auxiliary app AP2 in the user interface terminal 130 communicates with the communication unit 263 and registers the pillow 260 of the user M in advance.

The cover 264 houses the multiple air cells 261, the driving unit 262*a*, the control unit 262*b*, and the communication unit 263. The cover 264 may further house a cushion member. Here, the control unit may be located outside the cover.

Next, the recommendation function of the auxiliary app AP2 is described.

The auxiliary app AP2 acquires the recommendation setting D22 of the mattress 110, the bed 250, and the pillow 260 from the server. The auxiliary app AP2 presents the recommendation setting D22 to the user M by displaying it on the display 131.

The recommendation setting D22 of the bed 250 includes the recommended angle of the back section 251*a*, the recommended angle of the upper leg section 251*b*, and the recommended angle of the lower leg section 251*c*, for example. The recommendation setting D22 of the pillow 260 includes the recommended height or recommended hardness of each of the air cells 261, for example. The auxiliary app AP2 may present a set of the recommendation setting D22 of the mattress 110, the bed 250, and the pillow 260, or may alternatively present multiple sets of the recommendation setting D22 in the order of recommendation.

The user M can determine setting D23 of the mattress 110, the bed 250, and the pillow 260 while referring to the recommendation setting D22. As illustrated in FIG. 9, the auxiliary app AP2 sends the setting D23 of the mattress 110, the bed 250, and the pillow 260 to the server 240. Note that, the user M may set the setting D3 of the mattress 110, the bed 250, and the pillow 260 not using the recommendation function of the auxiliary app AP2 but using the setting function thereof.

FIG. 11 is a chart illustrating data stored in the server in this embodiment.

As in the server 140 in the first embodiment, the server 240 has functions as the acquisition unit 141, the computation unit 142, the output unit 143, and the memory 144.

The memory 144 stores data TD2. The data TD2 has, for each user M, an item of the setting D23 of each of the mattress 110, the bed 250, and the pillow 260. The item of the setting D23 of the mattress 110 includes a hardness setting value item of each of the air cell units U1, U2, U3, U4, U5, and U6. The item of the setting D23 of the bed 250 includes an angle setting value item of each of the sections 251*a*, 251*b*, and 251*c*. The item of the setting D23 of the pillow 260 includes a height setting value item of each of the air cells 261. In addition, the data TD2 has an item of the sleep score D5 associated with each of the sets of the setting D23 of the mattress 110, the bed 250, and the pillow 260.

The computation unit 142 determines the recommendation setting D22 of the mattress 110, the bed 250, and the pillow 260 of the user M based on the input information of the user M and the sleep information.

Specifically, in this embodiment, the computation unit 142 sets, as the recommendation setting D22, the setting D23 associated with the high-level sleep score D5 among the sets of the setting D23 of the mattress 110, the bed 250, and the pillow 260 of the users M who belong to the same category CA as the user M requesting the recommendation setting D22. The output unit 143 outputs the recommendation setting D22 to the auxiliary app AP2 in the user interface terminal 130. However, the system may have such a configuration that the auxiliary app acquires the preferred setting, such as the preferred hardness of the mattress and the pillow, at the time of the user registration and the output unit outputs the recommendation setting based on the attribute information of the user, the preferred setting, and the sleep information. Alternatively, the output unit may output the recommendation setting based on the user's use record.

Next, the automatic operation mode selection function of the auxiliary app AP2 is described.

Figure 12:
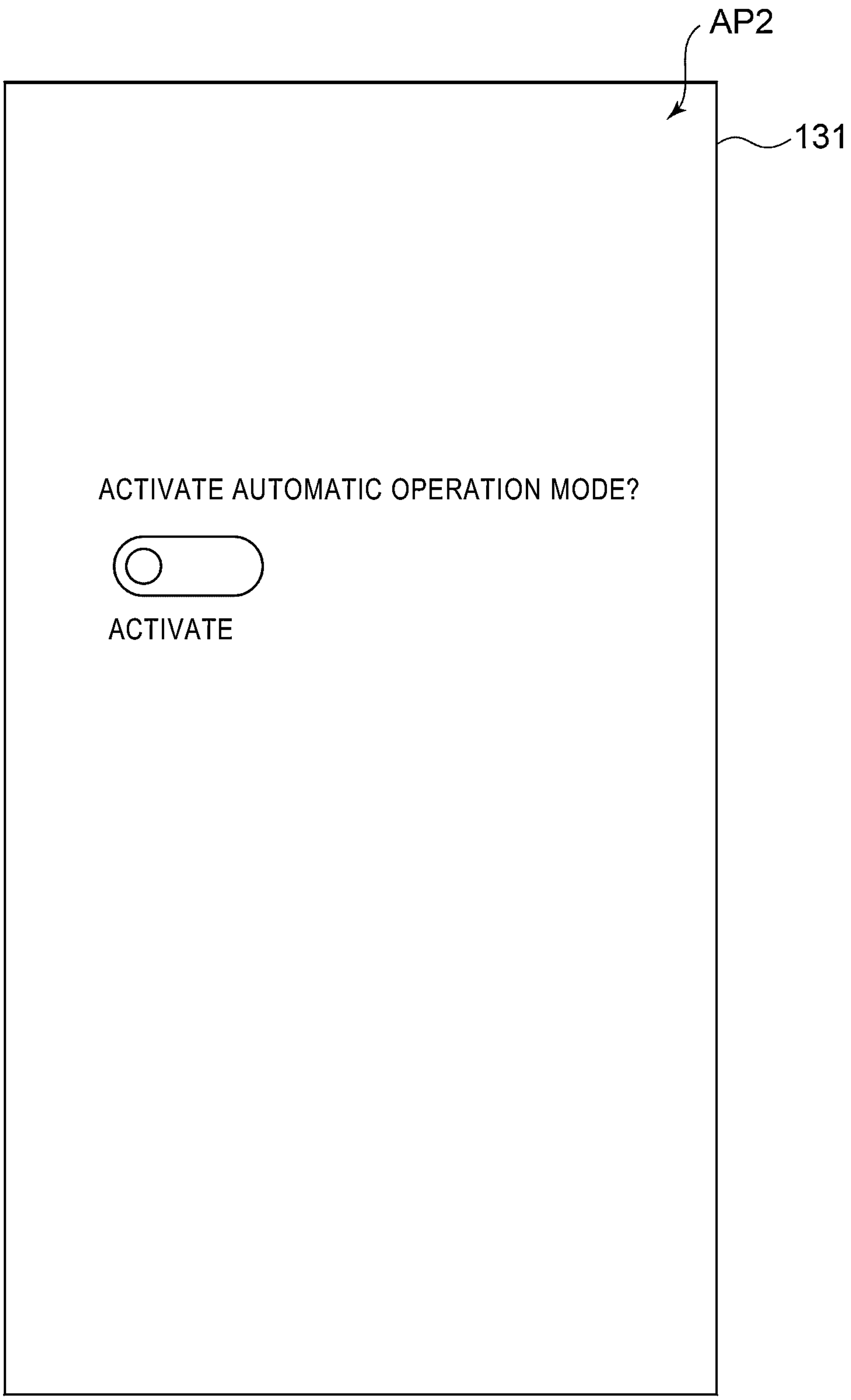
FIG. 12 is a diagram illustrating an automatic operation mode selection screen of the auxiliary app in the second embodiment.

FIG. 12 is a diagram illustrating an automatic operation mode selection screen of the auxiliary app in this embodiment.

The user M can select whether or not to activate the automatic operation mode of the mattress 110, the bed 250, and the pillow 260 on the auxiliary app AP2. The automatic operation mode is a mode of automatically changing the setting of the mattress 110, the bed 250, and the pillow 260 according to the detection information D4 of the detector 120.

For example, the detector 120 detects the state of the user M such as the state of going to bed, falling asleep, sleeping, being awake, or being away from the bed. In this embodiment, the detector 120 previously stores the operation setting on how to operate the mattress 110, the bed 250, and the pillow 260 based on the state, body motion, and posture of the user M. The detector 120 selects, from the operation setting previously stored, the operation setting according to the detected state, body motion, and posture of the user M. The detector 120 sends the operation setting thus selected to each of the mattress 110, the bed 250, and the pillow 260. A specific operation example of the mattress 110, the bed 250, and the pillow 260 is to be described later.

Note that, each of the mattress, the bed, and the pillow may previously store the operation setting. In this case, the control unit of each of the mattress, the bed, and the pillow selects the operation setting corresponding to the detection information D4 from the operation information previously stored, and controls the driving unit based on the operation setting thus selected.

Alternatively, the memory of the server may store the operation setting. In this case, the detector sends the detection information to the server. In this case, the computation unit of the server selects the operation setting corresponding to the detection information from the operation setting, and sends it to each of the mattress, the bed, and the pillow.

Next, operations of the motorized bedding system 200 according to this embodiment are described.

Figure 13:
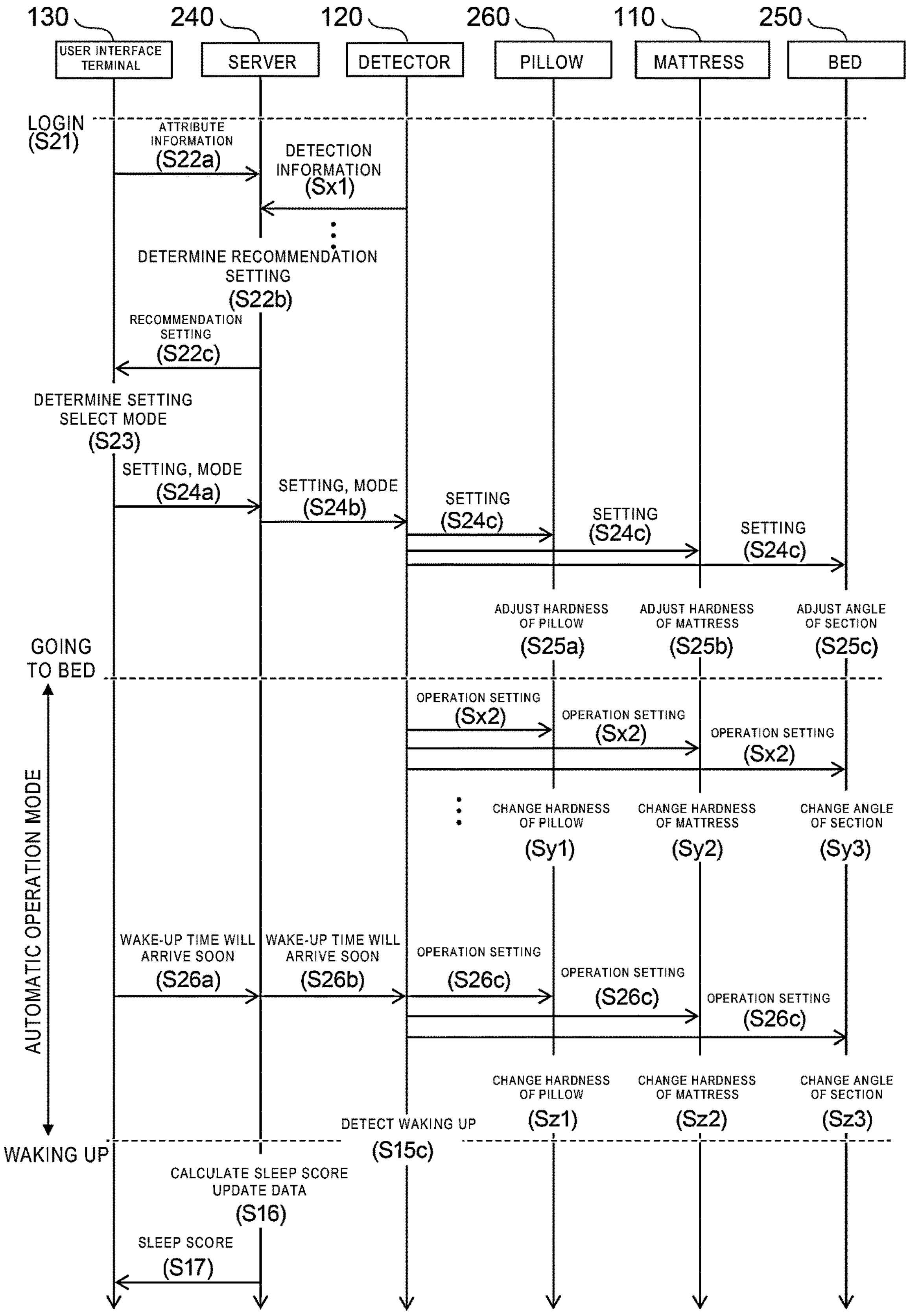
FIG. 13 is a sequence diagram illustrating operations of the motorized bedding system according to the second embodiment.

FIG. 13 is a sequence diagram illustrating the operations of the motorized bedding system according to this embodiment.

Note that, the operations of the motorized bedding system 200 described below are an example. The constituents executing the operations of the motorized bedding system, the timings at which these operations are executed, and the order in which these operations are executed can vary depending on the configuration of the motorized bedding system.

The user M logs into the auxiliary app AP in the user interface terminal 130 if wanting to set up the pillow 260, the mattress 110, and the bed 250 while referring to the recommendation function of the auxiliary app AP2 (Step S21).

Next, the user interface terminal 130 sends the identification information D1*a* and attribute information D1*b* of the user M to the server 240 (Step S22*a*). However, the user interface terminal may alternatively send only the identification information.

Subsequently, the computation unit 142 of the server 240 determines the recommendation setting D22 of the pillow 260, the mattress 110, and the bed 250 based on the input information of the user M and the sleep information (Step S22*b*).

Next, the output unit 143 of the sever 240 sends the recommendation setting D22 of the pillow 260, the mattress 110, and the bed 250 to the user interface terminal 130 (Step S22*c*).

Subsequently, the auxiliary app AP2 in the user interface terminal 130 displays the recommendation setting D22 of the pillow 260, the mattress 110, and the bed 250 on the display 131 to make the user M determine the setting D23 of the pillow 260, the mattress 110, and the bed 250 (Step S23). In addition, the auxiliary app AP2 makes the user M input whether or not to activate a mode such as the automatic operation mode. The following description provides an example in which the automatic operation mode is activated. However, the user M may deactivate the automatic operation mode.

Next, the auxiliary app AP2 sends the setting D23 of the pillow 260, the mattress 110, and the bed 250 to the server 240 (Step S24*a*). In addition, the auxiliary app AP2 sends the server 240 the user M's mode input result including the result that the automatic operation mode is activated. The acquisition unit 141 of the server 240 updates the data TD2 so that the setting D23 of the pillow 260, the mattress 110, and the bed 250 is associated with the identification information D1*a* of the corresponding user M.

Subsequently, the output unit 143 of the server 240 sends the setting D23 of the pillow 260, the mattress 110, and the bed 250 to the detector 120 (Step S24*b*).

Next, the detector 120 sends the setting D23 of the pillow 260 to the pillow 260 (Step S24*c*). In addition, the detector 120 sends the setting D23 of the mattress 110 to the mattress 110. Further, the detector 120 sends the setting D23 of the bed 250 to the bed 250.

Subsequently, the control unit 262*b* of the pillow 260 controls the driving unit 262*a* based on the setting D23 to adjust the hardness of each of the air cells 261 (Step S25*a*). In addition, the control unit 112*b* of the mattress 110 controls the driving unit 112*a* based on the setting D23 to adjust the hardness of each of the air cell units U1, U2, U3, U4, U5, and U6 (Step S25*b*). Further, the control unit 252*b* of the bed 250 controls the driving unit 252*a* based on the setting D23 to adjust the angle of each of the sections 251*a*, 251*b*, and 251*c* (Step S25*c*). Next, the user M gets onto the mattress 110.

In the subsequent process, if the automatic operation mode is activated, the detector 120 sets the operation of the pillow 260 according to the detection information D4, and sends the operation setting of the pillow 260 to the pillow 260 (Step Sx2). Likewise, in this case, the detector 120 sets the operation of the mattress 110 according to the detection information D4, and sends the operation setting of the mattress 110 to the mattress 110 (Step Sx2). Likewise, in this case, the detector 120 sets the operation of the bed 250 according to the detection information D4, and sends the operation setting of the bed 250 to the bed 250 (Step Sx2).

The control unit 262*b* of the pillow 260 controls the driving unit 262*a* according to the operation setting to change the hardness of each of the air cells 261 (Step Sy1). In addition, the control unit 112*b* of the mattress 110 controls the driving unit 112*a* according to the operation setting to change the hardness of each of the air cell units U1, U2, U3, U4, 5, and U6 (Step Sy2). Further, the control unit 252*b* of the bed 250 controls the driving unit 252*a* according to the operation setting to change the angle of each of the sections 251*a*, 251*b*, and 251*c* (Step Sy3).

Hereinbelow, a specific example of the control in the automatic operation mode is described.

For example, if the detector 120 detects that the user M stays awake after a predetermined period has passed since the user went to bed, the control unit 262*b* of the pillow 260 may control the driving unit 262*a* to soften the pillow 260. In addition, in this case, the control unit 112*b* of the mattress 110 may control the driving unit 112*a* to soften the mattress 110. Further, in this case, the control unit 252*b* of the bed 250 may control the driving unit 252*a* to increase the angle of the back section 251*a* to the set angle. The set angle is not particularly limited to a specific angle, but is equal to or larger than 10 degrees, for example. This facilitates the user M falling asleep. Note that, irrespective of whether or not the user is awake, each of these control units may perform the above control at the timing when the detector 120 detects that a predetermined period has passed since the user went to bed.

If the detector 120 detects that the user M has fallen asleep, the control unit 112*b* of the mattress 110 may control the driving unit 112*a* to put the hardness of the mattress 110 back to the original hardness. In addition, the control unit 252*b* of the bed 250 may control the driving unit 252*a* to put the angle of the back section 251*a* back to the original angle. Further, the control unit 262*b* of the pillow 260 may control the driving unit 262*a* to put the hardness of the pillow 260 back to the original hardness. Note that, each of these control units may perform the control of putting the setting back to the original when the detector detects that the body motion is equal to or smaller than a threshold instead of when the detector detects that the user has fallen asleep.

Meanwhile, for example, if the detector 120 detects that the body motion of the user M during a predetermined period is equal to or smaller than a threshold, the control unit 262*b* of the pillow 260 may control the driving unit 262*a* to harden the pillow 260. In addition, in this case, the control unit 112*b* of the mattress 110 may control the driving unit

112*a* to harden the mattress 110. This can increase the number of body motions of the user M.

Meanwhile, for example, if the detector 120 detects that the user M is in a supine position, the driving unit 112*a* of the mattress 110, the driving unit 252*a* of the bed 250, and the driving unit 262*a* of the pillow 260 operate. Specifically, the control unit 112*b* of the mattress 110 controls the driving unit 112*a* so that the first air cell unit U1 becomes harder than the third air cell unit U3 and the fourth air cell unit U4. Thereby, the head part of the user M is raised whereas a waist part and the buttocks of the user sink into the mattress 110. In addition, the control unit 252*b* of the bed 250 controls the driving unit 252*a* so that the angle of the back section 251*a* increases. The angle of the back section 251*a* is not particularly limited to a specific angle, but is 30 degrees, for example. In this event, the control unit 262*b* controls the driving unit 252*a* so that the back section 251*a* moves at a low speed. Thereby, the back of the user M is raised. Further, the control unit 262*b* of the pillow 260 controls the driving unit 262*a* so that the height of the pillow 260 increases. Thereby, the head part of the user M is raised. Furthermore, the control unit 262*b* of the pillow 260 controls the driving unit 262*a* so that the air cells 261 on the neck side become higher than the air cells 261 on the head side. Thereby, the chin of the user M is raised.

Meanwhile, if the detector 120 detects that the user M is in a lateral position, the driving unit 112*a* of the mattress 110 and the driving unit 252*a* of the bed 250 operate and the driving unit 262*a* of the pillow 260 does not operate. In this case, as in the case of the supine position, the control unit 112*b* of the mattress 110 controls the driving unit 112*a* so that the first air cell unit U1 becomes harder than the third air cell unit U3 and the fourth air cell unit U4. In this event, the control unit 112*b* controls the driving unit 112*a* so that the hardness of each of the third air cell unit U3 and the fourth air cell unit U4 becomes harder than that in the case of the supine position. In addition, the control unit 252*b* of the bed 250 controls the driving unit 252*a* so that the angle of the back section 251*a* becomes smaller than that in the case of the supine position. The angle of the back section 251*a* is not particularly limited to a specific angle, but is 10 degrees, for example.

In the automatic operation mode, the operation of each of the driving units 112*a*, 252*a*, and 262*a* might awake the user M. To deal with this, each of the driving units 112*a*, 252*a*, and 262*a* may stop the operation if the detector 120 detects that at least one of the number of body motions, heart rate, and breathing rate of the user M changes by a value equal to or larger than a threshold from an average value obtained before the operation. This inhibits the user M from being awakened.

When each of the driving units 112*a*, 252*a*, and 262*a* stops the operation, the detector 120 may send the server 240 the event that each of the driving units 112*a*, 252*a*, and 262*a* has stopped the operation. When outputting the recommendation setting D22, the server 240 may determine the recommendation setting D22 so as not to select the setting of the mattress 110, the bed 250, and the pillow 260 observed at the timing when their operations have stopped during the automatic operation mode.

Meanwhile, in the automatic operation mode, each of the driving units 112*a*, 252*a*, and 262*a* may restart the operation if the detector 120 detects that at least one of the number of body motions, heart rate, and breathing rate of the user M no longer changes by a value equal to or larger than the threshold from the average value obtained before the operation. In the automatic operation mode, the server 240 may recommend deactivating the automatic operation mode if the number of times each of the driving units 112*a*, 252*a*, and 262*a* stops the operation exceeds a certain threshold or if the frequency at which the user M is awakened exceeds a threshold.

Meanwhile, the wake-up time may be set in the auxiliary app AP2 of the user interface terminal 130, for example. In this case, the auxiliary app AP2 sends the server 240 the event that the wake-up time will arrive soon (Step S26*a*). Subsequently, the server 240 sends the detector 120 the event that the wake-up time will arrive soon (Step S26*b*). If the detector 120 detects after Step S26*b* that the body motion of the user M increases, the detector 120 sends the operation setting for the pre-wakeup state to each of the pillow 260, the mattress 110, and the bed 250 (Step S26*c*).

Next, the control unit 262*b* of the pillow 260 controls the driving unit 262*a* according to the operation setting to adjust each of the air cells 261 so that the air cells become harder (Step Sz1). In addition, the control unit 112*b* of the mattress 110 controls the driving unit 112*a* according to the operation setting to adjust each of the air cell units U1, U2, U3, U4, U5, and U6 so that the air cell units become harder (Step Sz2). This facilitates the user M rolling over. The control unit 252*b* of the bed 250 controls the driving unit 252*a* according to the operation setting to move the back section 251*a* for back raising (Step Sz3). This facilitates the user M waking up.

The subsequent process is the same as that of the motorized bedding system 100 according to the first embodiment. Note that, the method of changing the setting of the mattress, the bed, and the pillow in the automatic operation mode is not limited to the above method.

As has been described above, the motorized bedding system 200 according to this embodiment presents the recommendation setting D22 of the mattress 110, the bed 250, and the pillow 260 based on the input information of the user M and the sleep information. Thus, the user M can set the mattress 110, the bed 250, and the pillow 260 easily while referring to the recommendation setting D22. In addition, by employing the recommendation setting D22, the user M is more likely to achieve high quality sleep. Accordingly, the motorized bedding system 200 can offer high quality sleep to the user M.

In addition, in the motorized bedding system 200 according to this embodiment, the mattress 110, the bed 250, and the pillow 260 are capable of operating according to the detection information D4 of the detector 120. Thereby, the motorized bedding system 200 can offer high quality sleep to the user M.

Note that, although the auxiliary app AP has the recommendation function in this embodiment, the auxiliary app does not necessarily have to have the recommendation function.

Third Embodiment

Next, a third embodiment is described.

Figure 14:
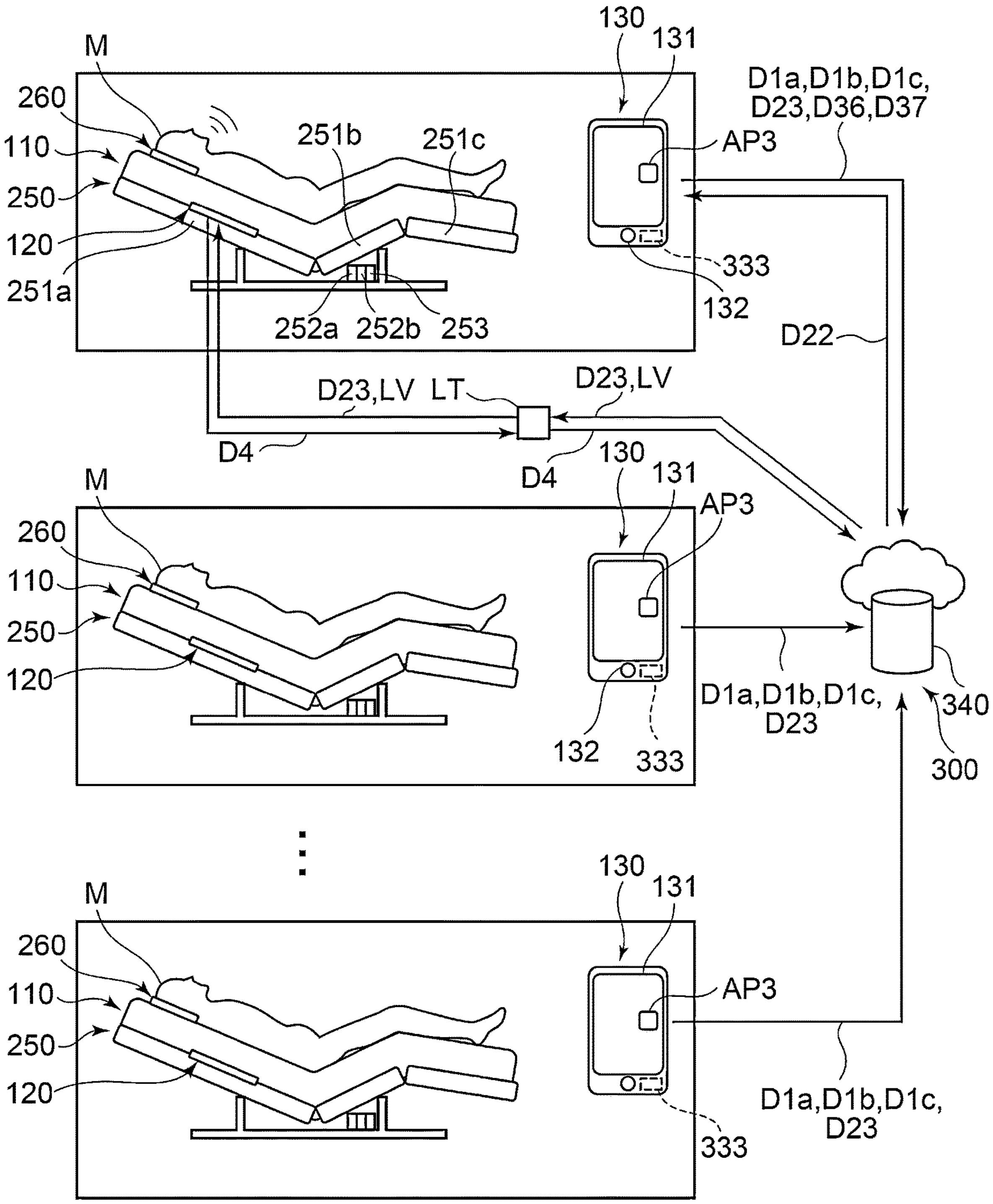
FIG. 14 is a conceptual diagram illustrating a motorized bedding system according to a third embodiment.

FIG. 14 is a conceptual diagram illustrating a motorized bedding system according to this embodiment.

Figure 15:
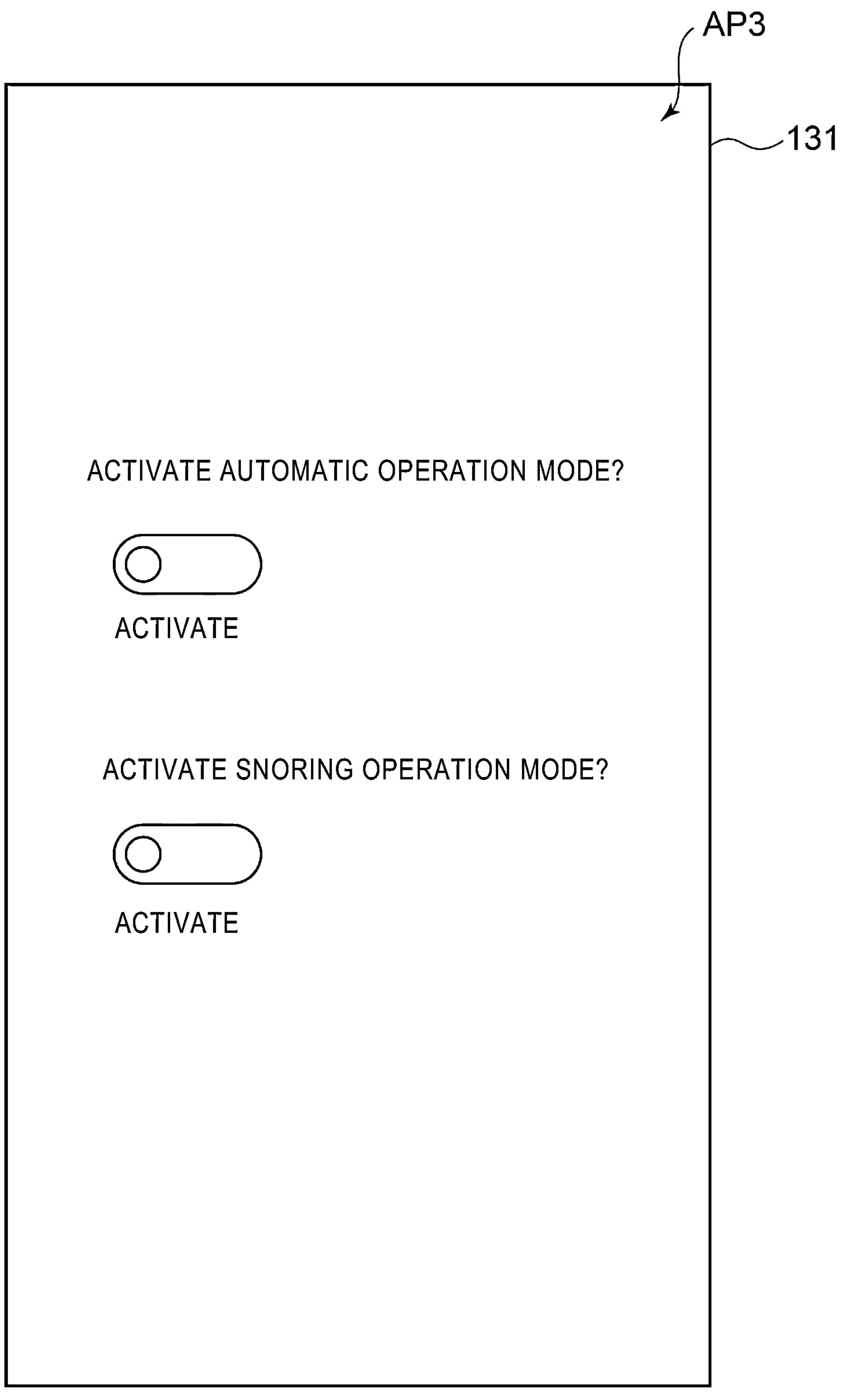
FIG. 15 is a diagram illustrating a snoring operation mode selection screen of the auxiliary app according to the third embodiment.

FIG. 15 is a diagram illustrating a snoring operation mode selection screen of the auxiliary app according to this embodiment.

A motorized bedding system 300 according to this embodiment differs from the motorized bedding system 200 according to the second embodiment in that the user M can select the snoring operation mode (a second mode) on an auxiliary app AP3.

Note that, in the following description, basically only the points of difference from the second embodiment are described. Points other than those to be described below are the same as those of the second embodiment.

The motorized bedding system 300 includes a detector 333 that is capable of detecting snoring. The detector 333 is mounted on the user interface terminal 130, for example. The detector 333 includes a microphone, for example. The detector 333 is configured to judge whether or not the user M is snoring based on a temporal change in sound measured by the microphone. However, the mattress, the bed, the pillow, or the like may alternatively have a detector that detects snoring.

As illustrated in FIG. 15, the user M can judge whether or not to activate the snoring operation mode on the auxiliary app AP3. The snoring operation mode is a mode of automatically changing, when the detector 333 detects snoring of the user M, the setting of the pillow 260, the mattress 110, and the bed 250 so as to inhibit snoring.

However, the user M may alternatively select whether or not to activate an apnea operation mode or a snoring/apnea operation mode on the auxiliary app AP3. The apnea operation mode is a mode of causing the pillow 260, the mattress 110, and the bed 250 to operate, when the detector 120 detects the apnea state of the user M, so as to inhibit the apnea of the user M. Meanwhile, the snoring/apnea operation mode is a mode of causing the pillow 260, the mattress 110, and the bed 250 to operate, when the detector 333 detects the snoring of the user M or when the detector 120 detects the apnea state of the user M, so as to inhibit the snoring or apnea of the user M. Although a description is given of the snoring operation mode below, the snoring operation mode in the description may be replaced with the apnea operation mode or the snoring/apnea operation mode as needed.

As illustrated in FIG. 14, when the detector 333 detects that the user M's snoring has occurred, the auxiliary app AP3 sends a server 340 snoring detection information D36 including the event that the snoring has occurred and the result of measurement by the microphone. Meanwhile, when the detector 333 detects that the user M's snoring has stopped, the auxiliary app AP3 sends the server 340 detection information D37 including the event that the snoring has stopped.

As in the server 140 in the first embodiment, the server 340 has functions as the acquisition unit 141, the computation unit 142, the output unit 143, and the memory 144.

The computation unit 142 calculates, based on the snoring detection information D36, the magnitude of snoring, the number (frequency) of snoring events, and the duration of snoring. Specifically, the computation unit 142 calculates the magnitude of snoring based on the amplitude of the signal indicating the temporal change in sound measured by the microphone. In addition, the computation unit 142 calculates the number (frequency) of snoring events based on how many waveforms of sound, each corresponding to one snoring event, are included in the temporal change signal of sound that is measured by the microphone in a predetermined period. Further, the computation unit 142 calculates the duration of snoring based on a period during which each waveform of sound corresponding to one snoring event appears in the temporal change signal of sound measured by the microphone.

The computation unit 142 judges a snoring level LV based on the magnitude of snoring, the number (frequency) of snoring events, and the duration of snoring thus calculated. The following description provides an example in which the snoring level LV includes Level 1, Level 2 at which the snoring level is worse than at Level 1, and Level 3 at which the snoring level is worse than at Level 2. However, the number of snoring levels may be two, or alternatively may be four or more. Note that, the auxiliary app may judge the snoring level. In addition, the server and the auxiliary app do not necessarily have to judge the snoring level.

The output unit 143 sends the snoring level LV to the detector 120. The detector 120 previously stores the operation setting of the mattress 110, the bed 250, and the pillow 260 suitable for each snoring level LV. The detector 120 selects, from the operation setting thus stored, the operation setting of the mattress 110, the bed 250, and the pillow 260 suitable for the snoring level LV. At least one of the pillow 260, the mattress 110, and the bed 250 operates according to the snoring level LV. A specific operation method of the pillow 260, the mattress 110, and the bed 250 is to be described later.

Note that, each of the mattress, the bed, and the pillow may previously store the operation setting suitable for each snoring level. In this case, each of the mattress, the bed, and the pillow selects, from the operation setting thus stored, the operation setting suitable for the snoring level. Alternatively, the server may previously store the operation setting suitable for each snoring level. In this case, the server selects, from the operation setting thus stored, the operation setting suitable for the calculated snoring level. In addition, when the apnea operation mode or the snoring/apnea operation mode exists, the system may have such a configuration that, as in the case of snoring, the server judges an apnea level and each of the pillow, the mattress, and the bed operates according to the setting suitable for the apnea level.

Next, operations of the motorized bedding system 300 according to this embodiment are described.

Figure 16:
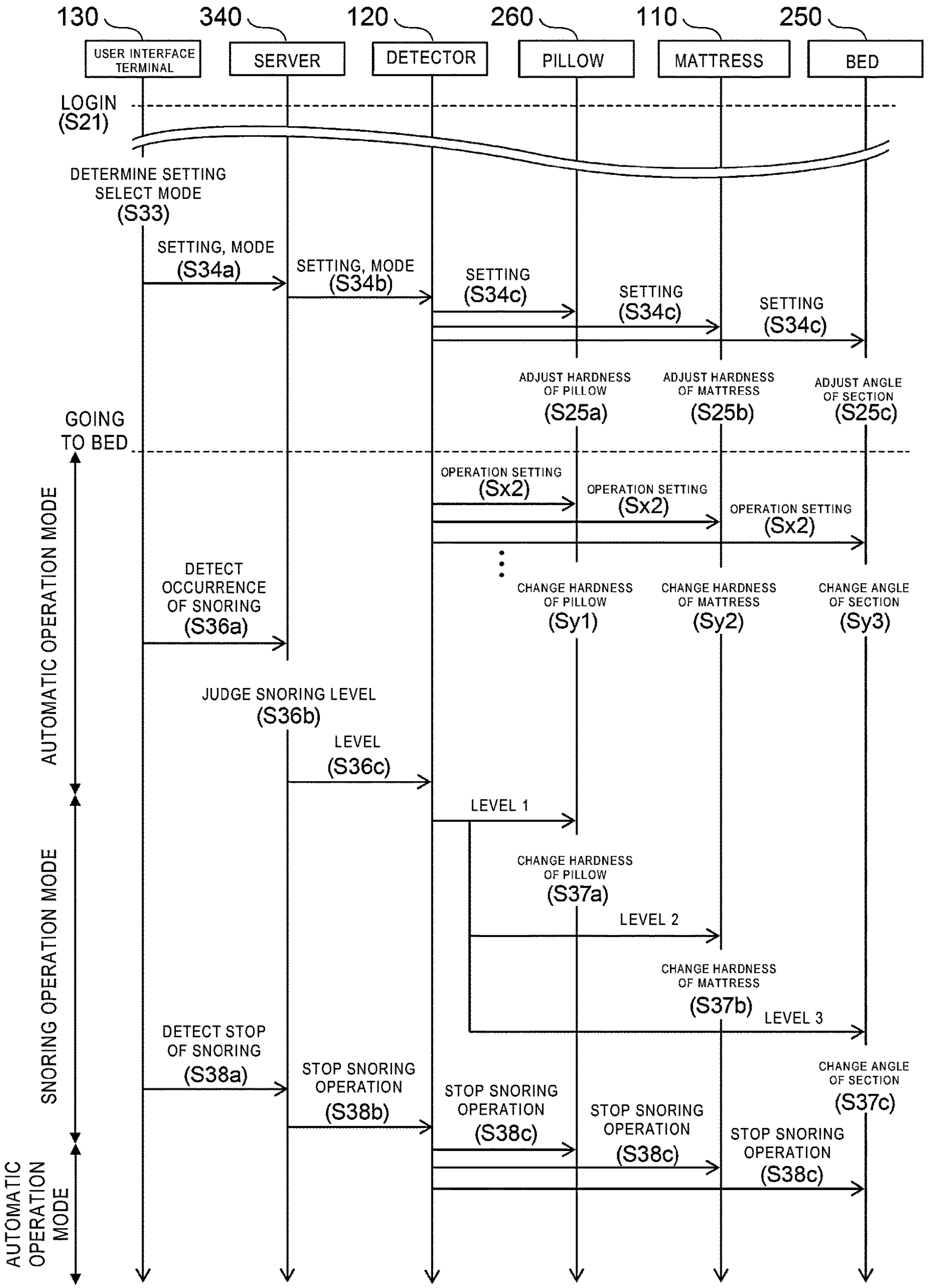
FIG. 16 is a sequence diagram illustrating operations of the motorized bedding system according to the third embodiment.

FIG. 16 is a sequence diagram illustrating the operations of the motorized bedding system according to this embodiment.

Note that, the operations of the motorized bedding system 300 described below are an example. The constituents executing the operations of the motorized bedding system, the timings at which these operations are executed, and the order in which these operations are executed can vary depending on the configuration of the motorized bedding system.

After receiving the recommendation setting D22 from the server 340, the auxiliary app AP3 displays the recommendation setting D22 on the display 131 to make the user M determine the setting D23 of the pillow 260, the mattress 110, and the bed 250 (Step S33). In addition, the auxiliary app AP3 makes the user M input whether or not to activate the automatic operation mode and the snoring operation mode. The following description provides an example in which both the automatic operation mode and the snoring operation mode are activated. However, the user M may deactivate the automatic operation mode or the snoring operation mode.

Next, the auxiliary app AP3 sends the setting D23 of the pillow 260, the mattress 110, and the bed 250 to the server 340 (Step S34*a*). In addition, the auxiliary app AP3 sends the server 340 the user M's mode input result including the result that the automatic operation mode and the snoring operation mode are activated. The acquisition unit 141 of the server 340 updates the data TD2 so that the setting D23 of the pillow 260, the mattress 110, and the bed 250 is associated with the identification information D1*a* of the corresponding user M.

Subsequently, the server 340 sends the detector 120 the setting D23 of the pillow 260, the mattress 110, and the bed 250 and the result that the automatic operation mode and the snoring operation mode are activated (Step S34*b*).

Next, the detector 120 sends the setting D23 of the pillow 260 to the pillow 260 (Step S34*c*). In addition, the detector 120 sends the setting D23 of the mattress 110 to the mattress 110. Further, the detector 120 sends the setting D23 of the bed 250 to the bed 250.

Subsequently, the control unit 262*b* of the pillow 260 controls the driving unit 262*a* based on the setting D23 to adjust the hardness of each of the air cells 261 (Step S25*a*). In addition, the control unit 112*b* of the mattress 110 controls the driving unit 112*a* based on the setting D23 to adjust the hardness of each of the air cell units U1, U2, U3, U4, U5, and U6 (Step S25*b*). Further, the control unit 252*b* of the bed 250 controls the driving unit 252*a* based on the setting D23 to adjust the angle of each of the sections 251*a*, 251*b*, and 251*c* (Step S25*c*). Next, the user M gets onto the mattress 110.

In the subsequent process, the motorized bedding system 300 basically gets into the automatic operation mode. If the user M snores during the automatic operation mode, the detector 333 detects the occurrence of snoring of the user M. In this case, the auxiliary app AP3 sends the snoring detection information D36 to the server 340 (Step S36*a*).

Next, the computation unit 142 of the server 340 judges the snoring level LV based on the snoring detection information D36 (Step S36*b*). Subsequently, the output unit 143 of the server 340 sends the detector 120 an instruction signal to switch the mode from the automatic operation mode to the snoring operation mode (Step S36*c*). In addition, the output unit 143 of the server 340 sends the snoring level LV to the detector 120. At least one of the driving unit 262*a* of the pillow 260, the driving unit 112*a* of the mattress 110, and the driving unit 252*a* of the bed 250 operates according to the snoring level LV received by the detector 120.

For example, if the snoring level LV is Level 1, the driving unit 262*a* of the pillow 260 operates so as to inhibit snoring (Step S37*a*). For example, the control unit 262*b* of the pillow 260 controls the driving unit 262*a* so that the height of the pillow becomes larger than that before the change. Meanwhile, if the snoring level LV is Level 2, the driving unit 112*a* of the mattress 110 operates so as to inhibit snoring (Step S37*b*). For example, the control unit 112*b* of the mattress 110 controls the driving unit 112*a* so that the height of each of the second air cell unit U2 and the third air cell unit U3 becomes larger than that before the change. Meanwhile, if the snoring level LV is Level 3, the driving unit 252*a* of the bed 250 operates so as to inhibit snoring (Step S37*c*). For example, the control unit 252*b* of the bed 250 controls the driving unit 252*a* so that the angle of the back section 251*a* becomes larger than that before the change.

If the snoring of the user M stops, the detector 333 detects the stop of the snoring of the user M. In this case, the auxiliary app AP3 sends the snoring stop detection information D37 to the server 340 (Step S38*a*). Next, the output unit 143 of the server 340 instructs the detector 120 to stop the snoring operation mode and change the mode to the automatic operation mode (Step S38*b*). Subsequently, the detector 120 instructs the mattress 110, the pillow 260, and the bed 250 to stop the snoring operation mode and change the mode to the automatic operation mode (Step S38*c*).

As has been described above, in the motorized bedding system 300 according to this embodiment, the user M can select whether or not to activate the snoring operation mode in the auxiliary app AP3. When the snoring operation mode is activated, if the detector 333 detects snoring of the user M, at least one of the mattress 110, the bed 250, and the pillow 260 automatically changes its setting so as to inhibit the snoring of the user M. Thus, the snoring of the user M can be inhibited. Thereby, the motorized bedding system 300 can offer high quality sleep to the user M.

In addition, in the case where both the automatic operation mode and the snoring operation mode are activated for a certain user M out of the multiple users M, upon acquiring the snoring detection information D36 of the certain user M, the motorized bedding system 300 prioritizes the snoring operation mode over the automatic operation mode for this user. Thus, the snoring of the user M can be inhibited. Thereby, the motorized bedding system 300 can offer high quality sleep to the user M.

Further, as bedding sets, the motorized bedding system 300 includes at least two of the mattress 110, the bed 250, and the pillow 260. When being set at the automatic operation mode, the motorized bedding system 300 automatically changes the setting of at least two of the bedding sets based on the state of each user M. Meanwhile, when being set at the snoring operation mode, the motorized bedding system 300 automatically changes the setting of at least one of the bedding sets out of the mattress 110, the bed 250, and the pillow 260 based on the snoring detection information D36 of each user M. Accordingly, in the automatic operation mode, the motorized bedding system 300 can change the posture of the user M by changing the setting of two bedding sets. Meanwhile, in the snoring operation mode, the motorized bedding system 300 can inhibit the user M from being awakened by changing the setting of one bedding set.

Furthermore, when being set at the snoring operation mode, the motorized bedding system 300 judges the snoring level LV based on the snoring detection information D36 of each user M and automatically changes the setting of the mattress 110, the bed 250, and the pillow 260 according to the snoring level LV. Thereby, the motorized bedding system 300 can inhibit the snoring of the user M efficiently.

Modification Example

Next, a modification example of the third embodiment is described.

Figure 17:
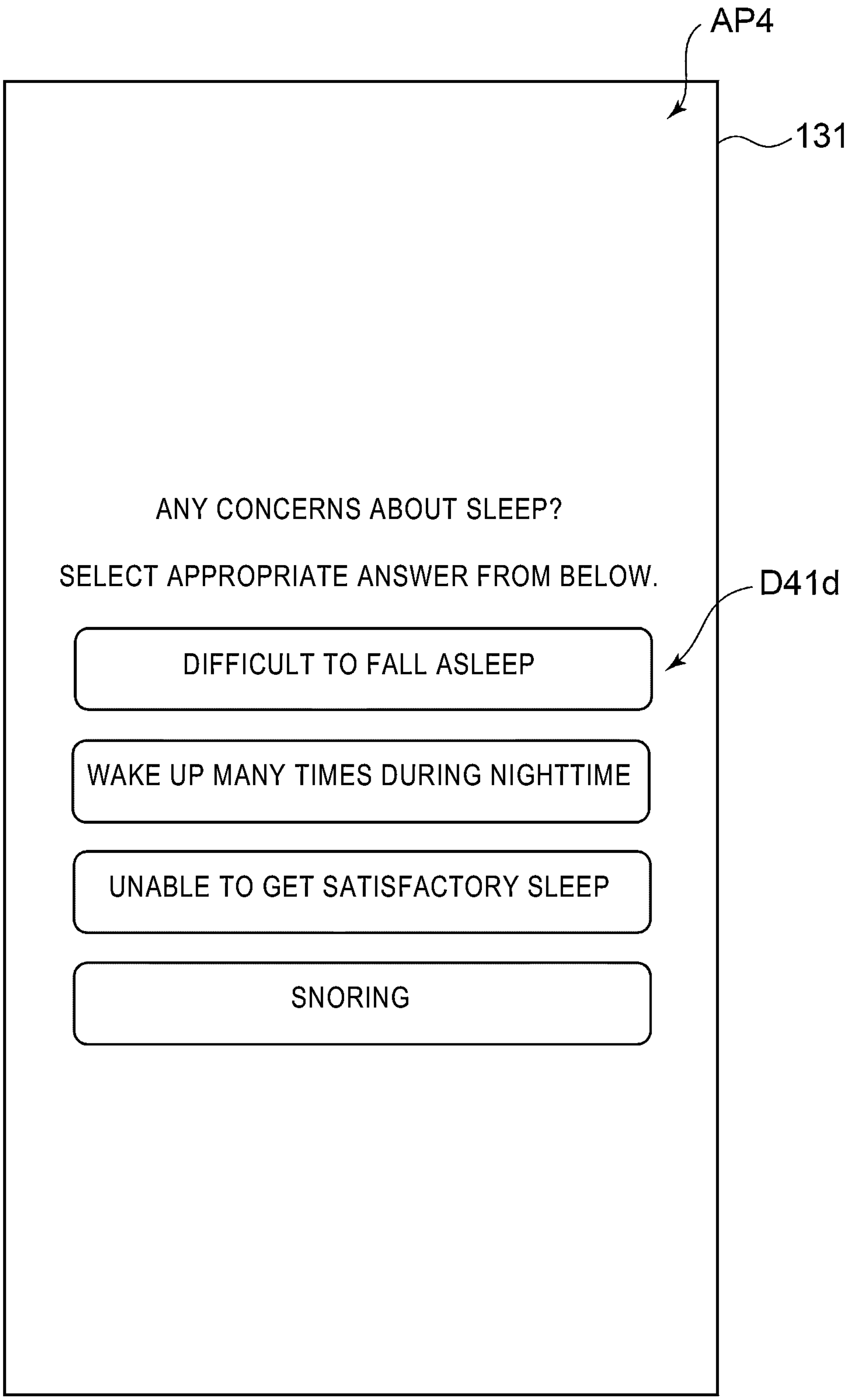
FIG. 17 is a diagram illustrating a user registration screen of the auxiliary app in a modification example.

FIG. 17 is a diagram illustrating a user registration screen of the auxiliary app in this modification example.

At the time of the user registration, an auxiliary app AP4 in the user interface terminal 130 may further acquire the user M's sleep feature information D41*d* as the sleep information. The user M's sleep feature information D41*d* includes the likelihood of snoring, for example. For example, the auxiliary app AP4 acquires the sleep feature information D41*d* by making the user M input information on whether or not items such as "difficult to fall asleep", "wake up many times during nighttime", "unable to get satisfactory sleep", and "snoring" apply.

In the automatic operation mode or the snoring operation mode, each of the mattress 110, the bed 250, and the pillow 260 may change the amount of change of the setting according to the sleep feature information D41*d*. Specifically, for the user M who is likely to snore, the control unit 112*b* of the mattress 110 may increase the amount of change of the hardness of the mattress 110. Likewise, the control unit 252*b* of the bed 250 may increase the amount of change of the angle of each of the sections 251*a*, 251*b*, and 251*c*.

Likewise, the control unit 262*b* of the pillow 260 may increase the amount of change of the hardness of each of the air cells 261.

In addition, the auxiliary app does not necessarily have to acquire the sleep feature information at the time of the user registration. Specifically, the server may presume the user's sleep feature based on the biological information acquired by the detector. Alternatively, the server may presume the user's sleep feature based on the body mass index included in the attribute information.

According to the embodiments, it is possible to provide the motorized bedding system capable of offering high quality sleep.

While the several embodiments have been described, these embodiments are provided as examples and are not for limiting the scope of this disclosure. These embodiments can be implemented in various modes other than those described above, and various omissions, replacements, and changes can be made without departing from the gist of this disclosure. These embodiments and their modifications are included in the scope and gist of this disclosure, and are included in the scope of the subject matters described in the scope of clams and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A system for an electric bed comprising:

an acquisition unit capable of obtaining each setting of an electric bed device for a plurality of users and each user's status;

a calculation unit configured to compute a sleep score based on each user's status;

a memory configured to store data associating the sleep score with each setting of the electric bed device; and an output unit configured to output a recommendation of the setting of the electric bed device based on the settings corresponding to the highest sleep scores among the multiple sleep scores stored in the memory, wherein the system includes a first mode where the system automatically changes the setting of the electric bed based on each user's status.

2. The system according to claim 1, wherein the electric bed device further comprises: an air mattress including a plurality of air cells, and wherein the recommendation of the setting of the electric bed device includes a firmness of the plurality of air cells.

3. The system according to claim 1, wherein the system further includes a second mode where the system automatically changes the setting of the electric bed device based on snoring detection information of each of the users.

4. The system according to claim 2, wherein the system further includes a second mode where the system automatically changes the setting of the electric bed device based on snoring detection information of each of the users.

5. The system according to claim 1, wherein the acquisition unit is configured to obtain attribute information of each user and the data being classified into a plurality of categories based on the attribute information, and the output unit is configured to output the recommendation of the setting of the electric bed device for a first user based on the setting of another user belonging to the same category as the first user among the plurality of users.

6. The system according to claim 4, wherein the acquisition unit is configured to obtain attribute information of each user and the data being classified into a plurality of categories based on the attribute information, and the output unit is configured to output the recommendation of the setting of the electric bed device for a first user based on the setting of another user belonging to the same category as the first user among the plurality of users.

7. The system according to claim 6, wherein the system is configured to prioritize the second mode over the first mode for the first user if the acquisition unit obtains the snoring detection information of the first user.

8. The system according to claim 5, wherein the acquisition unit is configured to obtain a preferred setting of the electric bed device for each user, and the data further includes the preferred setting of the electric bed device for each user, and the output unit is configured to output the recommendation of the setting of the electric bed device based on the settings of the electric bed devices of other users who belong to the same category as the first user and have the same preferred setting for the electric bed device, among the plurality of users.

9. The system according to claim 7, wherein the acquisition unit is configured to obtain a preferred setting of the electric bed device for each user, and the data further includes the preferred setting of the electric bed device for each user, and the output unit is configured to output the recommendation of the setting of the electric bed device based on the settings of the electric bed devices of other users who belong to the same category as the first user and have the same preferred setting for the electric bed device, among the plurality of users.

10. A method for controlling an electric bed comprising:

obtaining each setting of an electric bed device for a plurality of users and each user's status;

computing a sleep score based on each user's status;

storing, in memory, data associating the sleep score with each setting of the electric bed device;

outputting a recommendation of the setting of the electric bed device based on the settings corresponding to the highest sleep scores among the multiple sleep scores stored in the memory; and in a first mode, automatically changing the setting of the electric bed based on each user's status.

11. The method according to claim 10, wherein the recommendation of the setting of the electric bed device includes a firmness of a plurality of air cells in an air mattress.

12. The method according to claim 10, further comprising:

in a second mode, automatically changing the setting of the electric bed device based on snoring detection information of each of the users.

13. The method according to claim 11, further comprising:

in a second mode, automatically changing the setting of the electric bed device based on snoring detection information of each of the users.

14. The method according to claim 10, further comprising:

obtaining attribute information of each user and classifying the data into a plurality of categories based on the attribute information, and outputting the recommendation of the setting of the electric bed device for a first user based on the setting of another user belonging to the same category as the first user among the plurality of users.

15. The method according to claim 13, further comprising:

obtaining attribute information of each user and classifying the data into a plurality of categories based on the attribute information, and outputting the recommendation of the setting of the electric bed device for a first user based on the setting of another user belonging to the same category as the first user among the plurality of users.

16. The method according to claim 15, further comprising prioritizing the second mode over the first mode for the first user if the snoring detection information of the first user is obtained.

17. The method according to claim 14, further comprising:

obtaining a preferred setting of the electric bed device for each user, and the data further includes the preferred setting of the electric bed device for each user, and outputting the recommendation of the setting of the electric bed device based on the settings of the electric bed devices of other users who belong to the same category as the first user and have the same preferred setting for the electric bed device, among the plurality of users.

18. The method according to claim 16, further comprising:

obtaining a preferred setting of the electric bed device for each user, and the data further includes the preferred setting of the electric bed device for each user, and outputting the recommendation of the setting of the electric bed device based on the settings of the electric bed devices of other users who belong to the same category as the first user and have the same preferred setting for the electric bed device, among the plurality of users.

* * * * *